US012567479B2

(12) United States Patent
Lim et al.

(10) Patent No.: US 12,567,479 B2
(45) Date of Patent: Mar. 3, 2026

(54) METHOD AND APPARATUS FOR DETERMINING COPY NUMBER VARIATION PROFILE USING READ DEPTH CORRECTION IN WHOLE GENOME SEQUENCING

(71) Applicant: Inocras Korea Inc., Daejeon (KR)

(72) Inventors: Joonoh Lim, Daejeon (KR); Seongyeol Park, Daejeon (KR)

(73) Assignee: Inocras Korea Inc., Daejeon (KR)

( * ) Notice: Subject to any disclaimer, the term of this patent is extended or adjusted under 35 U.S.C. 154(b) by 0 days.

(21) Appl. No.: 18/507,755

(22) Filed: Nov. 13, 2023

(65) Prior Publication Data

US 2025/0022534 A1    Jan. 16, 2025

(30) Foreign Application Priority Data

Jul. 11, 2023    (KR) ......................... 10-2023-0089653

(51) Int. Cl.
G16B 20/10    (2019.01)
(52) U.S. Cl.
CPC .................................... G16B 20/10 (2019.02)
(58) Field of Classification Search
None
See application file for complete search history.

(56) References Cited

U.S. PATENT DOCUMENTS

2022/0336046 A1    10/2022    Zhu et al.

FOREIGN PATENT DOCUMENTS

CN    113674803 A    11/2021

OTHER PUBLICATIONS

Suvakov, Milovan, et al. "CNVpytor: a tool for copy number variation detection and analysis from read depth and allele imbalance in whole-genome sequencing." Gigascience 10.11 (2021): giab074. (Year: 2021).*
Scheinin, Ilari, et al. "DNA copy number analysis of fresh and formalin-fixed specimens by shallow whole-genome sequencing with identification and exclusion of problematic regions in the genome assembly." Genome research 24.12 (2014): 2022-2032. (Year: 2014).*
Smolander, Johannes, et al. "Evaluation of tools for identifying large copy number variations from ultra-low-coverage whole-genome sequencing data." BMC genomics 22.1 (2021): 357. (Year: 2021).*
Pique-Regi, Roger, et al. "Detecting changes in DNA copy number Reviewing signal processing techniques." IEEE Signal Processing Magazine 29.1 (2011): 98-107. (Year: 2011).*

(Continued)

*Primary Examiner* — Karlheinz R. Skowronek
*Assistant Examiner* — Mary C Leverett
(74) *Attorney, Agent, or Firm* — Banner & Witcoff, Ltd.

(57)    ABSTRACT

The present disclosure relates to a method for determining a copy number variation profile, which is executed by one or more processors, and includes acquiring results of whole-genome analysis associated with a target sample collected from a subject, calculating a read depth associated with the target sample for each of a plurality of predetermined bins on genome based on the acquired results of whole-genome analysis, correcting the read depth associated with the target sample, and determining a copy number variation profile associated with the target sample using the corrected read depth.

20 Claims, 13 Drawing Sheets

(56) References Cited

OTHER PUBLICATIONS

Chin, Suet-Feung, et al. "Shallow whole genome sequencing for robust copy number profiling of formalin-fixed paraffin-embedded breast cancers." Experimental and molecular pathology 104.3 (2018): 161-169. (Year: 2018).*

Abyzov, Alexej, et al. "CNVnator: an approach to discover, genotype, and characterize typical and atypical CNVs from family and population genome sequencing." Genome research 21.6 (2011): 974-984. (Year: 2011).*

Mendez, Pedro et al., Systematic comparison of two whole-genome amplification methods for targeted next-generation sequencing using frozen and FFPE normal and cancer tissues, Scientific Reports, Jun. 22, 2017, vol. 7, No. 4055, pp. 1-10.

Kader, Tanjina et al., Copy number analysis by low coverage whole genome sequencing using ultra low-input DNA from formalin-fixed paraffin embedded tumor tissue, Genome Medicine, Nov. 15, 2016, vol. 8, No. 121, pp. 1-13.

Rapti, Melivoia et al., CoverageMaster: comprehensive CNV detection and visualization from NGS short reads for genetic medicine applications, Briefings in Bioinformatics, Mar. 10, 2022, vol. 23, No. 2, pp. 1-8.

Xian Hua Gao, "Comparison of Fresh Frozen Tissue With Formalin-Fixed Paraffin-Embedded Tissue for Mutation Analysis Using a Multi-Gene Panel in Patients With Colorectal Cancer", Frontiers in Oncology, vol. 10, article 310, Mar. 13, 2020, pp. 1-8.

The extended European search report issued by the European Patent Office on Jun. 5, 2024, which corresponds to European Patent Application No. 23218970.4-1122 and is related to U.S. Appl. No. 18/507,755.

* cited by examiner

| Bin | FFPE 1 | FFPE 2 | ... | FFPE n | FF 1 | FF 2 | ... | FF n | DIRECTION OF CORRECTION | MAGNITUDE OF CORRECTION | CORRECTION COEFFICIENT |
|---|---|---|---|---|---|---|---|---|---|---|---|
| Bin 1 | Depth_111 | Depth_112 | ... | Depth_11n | Depth_211 | Depth_212 | ... | Depth_21n | -1 | 0.5 | -0.5 |
| Bin 2 | Depth_121 | Depth_122 | ... | Depth_12n | Depth_221 | Depth_222 | ... | Depth_22n | 0 | 0.3 | 0 |
| ... | ... | ... | ... | ... | ... | ... | ... | ... | ... | ... | ... |
| Bin n | Depth_1n1 | Depth_1n2 | ... | Depth_1nn | Depth_2n1 | Depth_2n2 | ... | Depth_2nn | 1 | 0.2 | 0.2 |

FFPE 1
FFPE 2
FFPE 3
FFPE 4
FFPE 5
FFPE 6
FFPE 7
FFPE 8
FFPE 9
FFPE 10
FFPE 11
FFPE 12
FFPE 13
FFPE 14
FFPE 15
FFPE 16
FFPE 17
FFPE 18
FFPE 19
FFPE 20
FFPE 21
FFPE 22
FFPE 23
FFPE 24
FFPE 25
FFPE 26
FFPE 27
FFPE 28
FFPE 29
FFPE 30

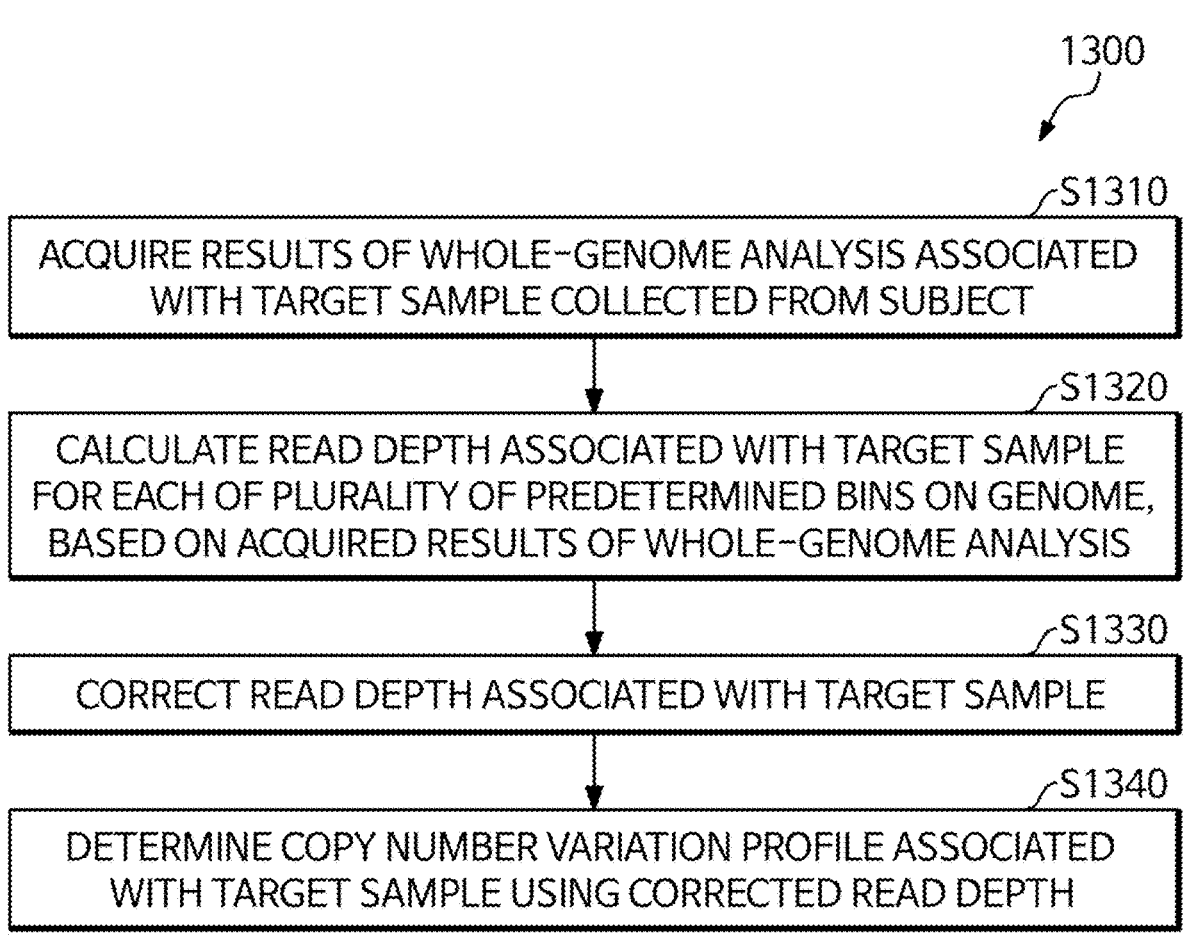

1300

S1310

ACQUIRE RESULTS OF WHOLE-GENOME ANALYSIS ASSOCIATED WITH TARGET SAMPLE COLLECTED FROM SUBJECT

S1320

CALCULATE READ DEPTH ASSOCIATED WITH TARGET SAMPLE FOR EACH OF PLURALITY OF PREDETERMINED BINS ON GENOME, BASED ON ACQUIRED RESULTS OF WHOLE-GENOME ANALYSIS

S1330

CORRECT READ DEPTH ASSOCIATED WITH TARGET SAMPLE

S1340

DETERMINE COPY NUMBER VARIATION PROFILE ASSOCIATED WITH TARGET SAMPLE USING CORRECTED READ DEPTH

METHOD AND APPARATUS FOR DETERMINING COPY NUMBER VARIATION PROFILE USING READ DEPTH CORRECTION IN WHOLE GENOME SEQUENCING

CROSS-REFERENCE TO RELATED APPLICATION

The present application claims the benefit of priority under 35 U.S.C. § 119 to Korean Patent Application No. 10-2023-0089653, filed in the Korean Intellectual Property Office on Jul. 11, 2023, the entire contents of which are hereby incorporated by reference.

TECHNICAL FIELD

The present disclosure relates to a method and apparatus for determining a copy number variation profile using read depth correction, and specifically, to a method and apparatus for determining a copy number variation profile by calculating and correcting a read depth associated with a target sample based on results of whole-genome analysis associated with the target sample collected from a subject.

BACKGROUND

Genetic information analysis technology is widely used in the medical field, for identifying genetic information of a living organism to determine its characteristics or traits, etc. In recent years, the approach to medical practice for understanding the cause of various diseases, such as tumors, or for treating diseases has transitioned from a traditional prescription-centric methodology to precision medicine. The precision medicine is a customized treatment modality that considers the genetic information, health records, etc. of individual patients. In the realm of precision medicine, acquiring a substantial amount of personal genetic information and performing clinical analysis associated with the same are crucial. These elements form the foundation that propels the advancement of the precision medicine technology.

In particular, the "Fresh Frozen (FF)" processing method is predominantly employed for whole-genome analysis of tissues collected from patients. This method involves immediate freezing of the tissues post-collection, preserving cellular integrity and minimizing DNA damage. However, this technique necessitates specific facilities or equipment, such as nitrogen tanks, which may not be readily available or are challenging to provide at the treatment site, for both processing and storage of the FF tissue.

Conversely, medical institutions commonly use the formalin-fixed, paraffin-embedded (FFPE) method for treating tissues (e.g., tumor tissues) collected from patients for genetic analysis. The tissues are subsequently stored for extended periods and utilized for follow-up testing or academic research. The FFPE method is cost-effective and requires minimal effort for tissue treatment and storage. Additionally, it enables long-term preservation of genetic information within the tissue, thus facilitating future use (e.g., for re-examination or re-analysis).

However, the FFPE treatment and prolonged storage can lead to various types of DNA damage within the tissues, including cross-linking (chemical entanglement of different DNA parts), fragmentation (breaking of DNA into smaller pieces), and variations in DNA bases due to non-biological factors.

Such DNA damage can introduce noise in the copy number variation (CNV) profile of the analysis data (raw data) when performing whole-genome analysis on FFPE treated tissue, potentially resulting in inaccurate and distorted results. Notably, this type of noise is generally absent in whole-genome analysis data derived from FF treated tissue. Consequently, it is imperative to effectively process or eliminate the noise in the CNV profile to obtain accurate analysis results from FFPE treated tissues.

SUMMARY

In order to solve the problems described above, the present disclosure provides a method, a recording medium, and an apparatus (system) for determining a copy number variation profile.

The present disclosure may be implemented in a variety of ways, including a method, a system (apparatus), or a computer program stored in a readable storage medium.

A method for determining a copy number variation profile using read depth correction is provided, which may be executed by one or more processors and include acquiring results of whole-genome analysis associated with a target sample collected from a subject, calculating a read depth associated with the target sample for each of a plurality of predetermined bins on genome based on the acquired results of whole-genome analysis, correcting the read depth associated with the target sample, and determining a copy number variation profile associated with the target sample using the corrected read depth.

The target sample may include a normal cell sample and an abnormal cell sample collected from the subject, and the determining the copy number variation profile may include determining the copy number variation profile based on the read depth associated with the normal cell sample, the read depth associated with the abnormal cell sample, and an allele frequency associated with the target sample.

The target sample may be a formalin-fixed, paraffin-embedded (FFPE) sample.

The correcting the read depth associated with the target sample may include performing a first correction of the read depth associated with the target sample using a data set including read depth data for each of the plurality of bins associated with each of a plurality of samples collected from a plurality of subjects different from the subject.

The data set may include at least one of data associated with a normal cell sample collected from each of the plurality of subjects or data associated with an abnormal cell sample collected from each of the plurality of subjects.

Each of the normal cell sample collected from each of the plurality of subjects and the abnormal cell sample collected from each of the plurality of subjects may include an FFPE sample and a fresh frozen (FF) sample.

The data set may further include information associated with a direction of correction of read depth for each of the plurality of bins, for use in correcting the read depth of the target sample.

The information associated with the direction of correction may be determined based on: for each of the plurality of bins, a distribution of read depths associated with all FFPE samples in the data set, and for each of the plurality of bins, a distribution of read depths associated with all FF samples in the data set.

The data set may further include information associated with a magnitude of correction of read depth for each of the plurality of bins, for use in correcting the read depth of the target sample.

The information associated with the magnitude of correction may be determined based on: for each of the plurality of bins, an average of read depths associated with all FFPE samples in the data set, and for each of the plurality of bins, an average of read depths associated with all FF samples in the data set.

The performing the first correction may include correcting a read depth associated with the target sample based on information associated with the direction of correction and information associated with the magnitude of correction.

The correcting the read depth associated with the target sample may further include performing a second correction to remove noise from the read depth that has been subject to the first correction.

The performing second correction to remove noise from the read depth may include determining a plurality of wavelet coefficients using a predetermined wavelet and the read depth that has been subject to the first correction, thresholding the plurality of wavelet coefficients, and determining a second corrected read depth based on the thresholded plurality of wavelet coefficients.

The predetermined wavelet may correspond to a Haar wavelet.

The thresholding the plurality of wavelet coefficients may include, if an absolute value of a specific wavelet coefficient of the plurality of wavelet coefficients is less than a predetermined threshold, replacing the specific wavelet coefficient with 0, and if the absolute value of the specific wavelet coefficient is greater than or equal to the threshold, attenuating the specific wavelet coefficient to a higher degree as a difference between the absolute value and the threshold decreases.

The threshold may be lower as the specific wavelet coefficients are higher-level wavelet coefficients.

There is provided a non-transitory computer-readable recording medium storing instructions for executing the method for determining the copy number variation profile on a computer.

An computing device is provided, which may include a communication module, a memory, and one or more processors connected to the memory and configured to execute one or more computer-readable programs included in the memory, in which the at least one program, may include instructions for acquiring results of whole-genome analysis associated with a target sample collected from a subject, calculating a read depth associated with the target sample for each of a plurality of predetermined bins on genome based on the acquired results of whole-genome analysis, correcting the read depth associated with the target sample, and determining a copy number variation profile associated with the target sample using the corrected read depth.

By grouping the genome into a plurality of bins, the instability of the read depth of the target sample due to noise (random noise or non-random noise) when calculating the read depth can be significantly reduced.

By hierarchically thresholding the detailed wavelet coefficients, the higher-level detailed wavelet coefficients containing information about the macroscopic shape of the signal are less likely to be replaced by zero or attenuated, such that the macroscopic copy number variation profile can be preserved as much as possible.

By correcting for noise or error that may occur when performing whole-genome analysis on FFPE tissue, undistorted analysis results can be derived as in whole-genome analysis data of FF tissue.

According to various examples of the present disclosure, whole-genome analysis can be performed with high accuracy on the vast amount of FFPE tissues ensured and accumulated by medical institutions, biobanks, etc., and whole-genome analysis of tissue samples from patients, etc. can be performed simply using the facilities provided at normal medical treatment sites without having to change the tissue sample treatment procedures at the medical institutions.

The effects of the present disclosure are not limited to the effects described above, and other effects not mentioned will be able to be clearly understood by those of ordinary skill in the art (referred to as "those skilled in the art") from the description of the claims.

BRIEF DESCRIPTION OF THE DRAWINGS

The above and other objects, features and advantages of the present disclosure will be described with reference to the accompanying drawings described below, where similar reference numerals indicate similar elements, but not limited thereto, in which:

FIG. 4 illustrates an example of a correction data set;

FIG. 5 illustrates a first correction process of a read depth associated with a target sample for each of a plurality of bins;

FIG. 8 illustrates examples of graphs and sets of coefficients utilized during the second correction;

FIG. 13 is a flowchart illustrating a method for determining a copy number variation profile.

DETAILED DESCRIPTION

Figure 1:
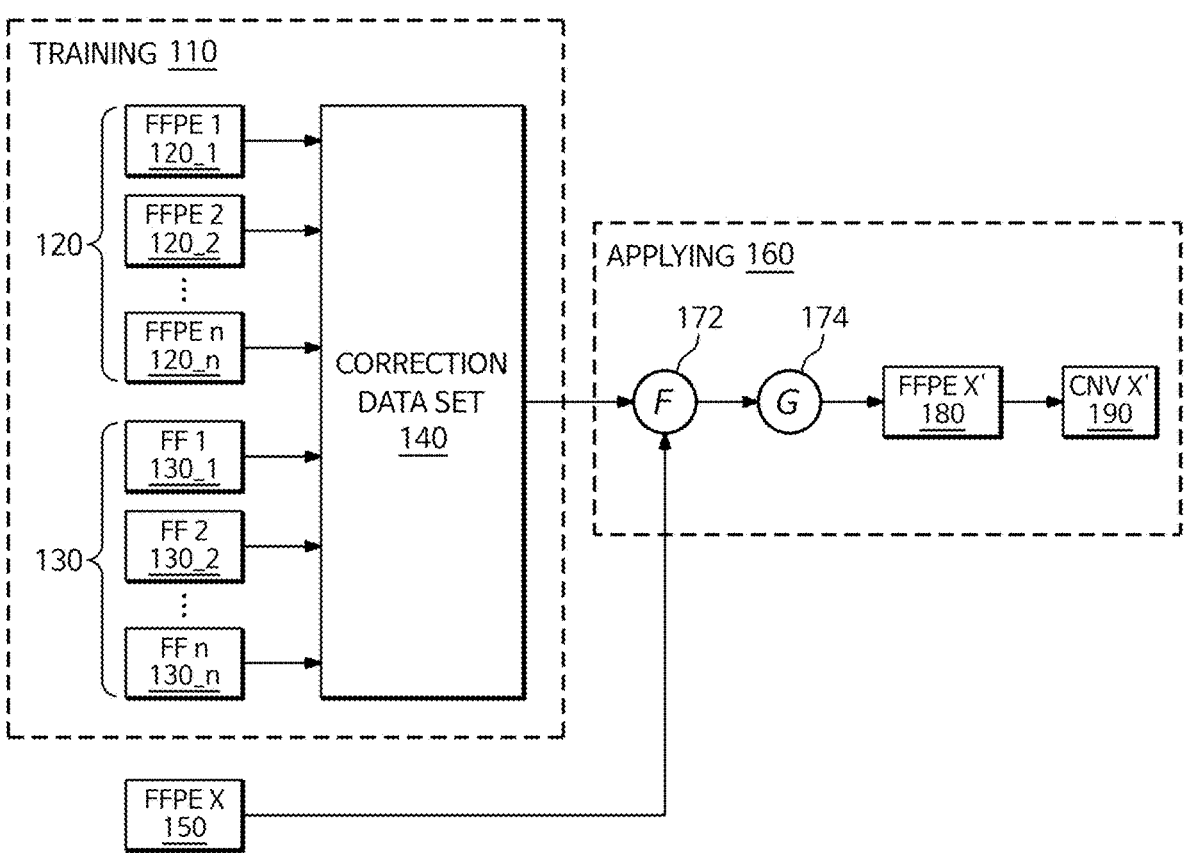
FIG. 1 illustrates detailed steps of a method for determining a copy number variation profile.

Hereinafter, example details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of components are omitted, it is not intended that such components are not included in any example.

Advantages and features of the disclosed examples and methods of accomplishing the same will be apparent by referring to examples described below in connection with the accompanying drawings. However, the present disclosure is not limited to the examples disclosed below, and may be implemented in various forms different from each other, and the examples are merely provided to make the present disclosure complete, and to fully disclose the scope of the disclosure to those skilled in the art to which the present disclosure pertains.

The terms used herein will be briefly described prior to describing the disclosed example(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the example(s). Therefore, the terms used in the present disclosure should be defined based on the meaning of the terms and the overall content of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it is intended as meaning that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play one or more processors. Accordingly, as an example, the "module" or "unit" may include components such as software components, object-oriented software components, class components, and task components, and at least one of processes, functions, attributes, procedures, subroutines, program code segments, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

The "module" or "unit" may be implemented as a processor and a memory. The "processor" should be interpreted broadly to encompass a general-purpose processor, a Central Processing Unit (CPU), a microprocessor, a Digital Signal Processor (DSP), a controller, a microcontroller, a state machine, etc. Under some circumstances, the "processor" may refer to an application-specific integrated circuit (ASIC), a programmable logic device (PLD), a field-programmable gate array (FPGA), etc. The "processor" may refer to a combination of processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EE-PROM), flash memory, magnetic or optical data storage, registers, etc. The memory is said to be in electronic communication with a processor if the processor can read information from and/or write information to the memory. The memory integrated with the processor is in electronic communication with the processor.

In the present disclosure, "subject" may refer to a patient, test subject, or any individual on whom a copy number variation profile determination according to the present disclosure will be performed.

In the present disclosure, "target sample" may refer to a sample obtained from a subject for which read depth is to be calculated and corrected for determining the copy number variation profile.

In the present disclosure, "bin" is a unit utilized for grouping or classifying at least a portion of the genome for gene/genome analysis, and may refer to a segment, etc. defined on the genome. The location or number of base sequences included in one bin, the number of bins, etc. may be determined arbitrarily or as one chooses. For example, considering a subject's genome comprising approximately 3 billion base pairs, around 3,000 bins may be designated, each encapsulating about 1 million bases.

In the present disclosure, "abnormal cell" may refer to a cell that is anomalous in aspects such as size, shape, structure, or function, when compared to a normal cell. The abnormal cells may arise due to various factors such as genetic variation, infections, exposure to toxins, and may encompass diverse types such as cancer cells, tumor cells, necrotic cells, senescent cells, aneuploid cells, hyperplastic cells, hypertrophic cells, and others.

In the present disclosure, the "read depth ratio" may refer to a ratio between a read depth obtained from sequencing a normal cell sample and a read depth obtained from sequencing an abnormal cell sample. Additionally, since the read depth may be calculated from the read depth ratio, the "read depth" may refer to the read depth ratio unless explicitly specified otherwise.

In the present disclosure, a "wavelet" or a "wavelet function" is a one-dimensional function that satisfies specific properties and may refer to a one-dimensional function that oscillates with negative and positive values starting from 0 in only one local area and whose integral value for all real numbers is 0. For example, the "wavelet" or "wavelet function" has $(-\infty, \infty)$ as its domain and may have a value of 0 in the area extending in negative and positive infinity directions outside the local area where oscillation appears. The wavelets or wavelet functions are classified according to the shape of oscillation, and include various types such as Haar, Daubechies, Coiflet, Best-localized Daubechies, Least asymmetric, etc.

FIG. 1 illustrates detailed steps of a method for determining a copy number variation profile. A method for determining a copy number variation profile may include training 110 and applying 160.

In the training 110, a correction data set 140 for correcting a target sample data 150 may be determined/trained based on an FFPE sample data set 120, which includes a plurality of FFPE sample data 120_1 to 120__n_, and an FF sample data set 130, which includes a plurality of FF sample data 130_1 to 130__n_, where n is a natural number. The FFPE sample data set 120 and the FF sample data set 130 may include data calculated from a plurality of samples collected from a plurality of different subjects, distinct from the subject from which the target sample is collected. The "sample data" may include any data associated with the sample, such as a copy number variation (CNV) profile or read depth associated with the sample, and FFPE sample data may refer to data associated with formalin-fixed, paraffin-embedded (FFPE) samples and FF sample data may refer to data associated with fresh-frozen (FF) samples.

In some embodiments, the training 110 is a machine learning process using a neural network model. The neutral network model can be implemented as collections of nodes (neurons) that are connected in an acyclic graph. One type of neural network, a "feedforward network", can receive an input (a single vector) at its input layer of nodes, and, through a series of hidden layers, map the input to values in an output layer of nodes. Each layer in the network is made up of a set of neurons, where each neuron is fully connected to all neurons in the adjacent layer(s), and where neurons within a layer do not share any connections. If the network is modeling a classification, each of the nodes in the output layer may represent one of the possible classes to which an entity belongs, and the value of each output node may represent the probability that the input entity belongs to that class. A convolutional neural network (CNN) is another type of neural network model that can model feature detection by performing convolution operations on input data. For example, in image processing, a CNN may receive raw image data input and then output a set of feature maps representing abstractions of the raw data.

At least one of the plurality of FFPE sample data 120_1 to 120__n_ and at least one of the plurality of FF sample data 130_1 to 130__n_ may be data associated with the sample collected from the same subject. For example, the first FFPE sample data 120_1 and the first FF sample data 130_1 may be data associated with samples collected from a specific subject and treated, or processed, in different ways (FFPE, FF), and the plurality of FFPE sample data 120_1 to 120__n_ and the plurality of FF sample data 130_1 to 130__n_ may be data associated with samples collected from (n) subjects and processed in different ways.

Each of the FFPE sample data set 120 and the FF sample data set 130 may include data associated with normal cell samples collected from each of a plurality of subjects and/or data associated with abnormal cell samples collected from each of the plurality of subjects. For example, the first FFPE sample data 120_1 and the first FF sample data 130_1 may be read depth data for each of a plurality of bins on a whole genome sequence obtained by analyzing a normal cell sample collected from a specific subject, and the second FFPE sample data 120_2 and the second FF sample data 130_2 may be read depth data for each of a plurality of bins on the whole genome sequence obtained by analyzing an abnormal cell sample collected from the same subject.

The correction data set 140 may include both the FFPE sample data set 120 and the FF sample data set 130. For example, the correction data set 140 may include the read depth data associated with the normal cell sample and the abnormal cell sample collected from each of a plurality of subjects different from the subject. Conversely, if the FFPE sample data set 120 or the FF sample data set 130 includes a copy number variation profile rather than the read depth data for each sample, a separate process for determining the read depth data from the copy number variation profile may be executed.

The target sample data 150 may be data (e.g., copy number variation profile, read depth data, etc.) associated with a target sample of a subject, which is to be corrected according to the present disclosure. For example, the target sample data 150 may be a read depth associated with the target sample calculated for each of a plurality of bins based on the results of whole-genome analysis associated with the target sample collected from the subject. At this time, the results of whole-genome analysis may include sequence data obtained by mapping and aligning read data obtained using a typical paired-end sequencing technique to the reference genome hg19, hg38, GRCh37, GRCh38, etc. through various sequencing data processing tools, etc. The target sample may include a normal cell sample and/or an abnormal cell sample collected from the subject.

In some embodiments, the whole-genome analysis can be performed through a combination of wet-lab and dry-lab procedures, encompassing pre-sequencer processing and post-sequencer processing, respectively.

Wet-lab procedures may include: i) Specimen Preparation, in which laboratory technician or clinical staff collects the patient's tissue or blood sample; ii) DNA Extraction, in which laboratory technician extracts DNA from the sample using laboratory techniques and relevant lab equipment; iii) Library Preparation, in which molecular biologist or laboratory technician fragments the DNA and prepares DNA libraries by adding sequencing adapters using lab equipment; and iv) Sequencing, in which sequencing technician performs high-throughput sequencing using a sequencer equipment (e.g., Illumina or MGI sequencers), generating raw sequencing data.

Dry-lab procedures may include: i) Conversion of Raw Sequencing Data into FASTQ File, in which computing devices equipped with bioinformatics tools are used to convert sequencer-specific raw sequencing data to standardized FASTQ files; ii) Alignment and BAM File Generation, in which computing devices equipped with bioinformatics tools like BWA or Bowtie to align the sequencing reads (e.g., FASTQ data) to a reference genome (e.g., GRCh38). SAM files are generated during this step, which are then converted to BAM files; iii) Marking Duplicates, in which computing devices equipped with bioinformatics tools to mark duplicate reads in the BAM file to account for PCR duplicates; iv) Coverage Calculation, in which computing devices equipped with bioinformatics tools calculates read coverage across the genome by counting reads aligned to each genomic region or bin (e.g., 1-kilobase bins), and coverage information is stored in separate files, such as BED or bigWig files; v) Quality Control, in which computing devices equipped with bioinformatics tools evaluates the quality of the BAM file and coverage data, checking alignment rates, coverage distribution, and duplicate rates; vi) Copy Number Profile Analysis, in which computing devices equipped with CNV analysis tools and algorithms (e.g., Sequenza or ASCAT) to detect copy number alterations. This step involves data analysis and statistical processing. The target sample may be a formalin-fixed, paraffin-embedded (FFPE) sample, and with the FFPE method, noise in the copy number variation profile (or, read depth) during whole genome analysis is removed according to the present disclosure, resulting in substantially the same or similar analytical accuracy as if the target sample were FF processed and then analyzed.

For use in correcting the read depth of the target sample, the correction data set 140 may further include information associated with the direction and the magnitude of correction of the read depth, for each of the plurality of bins. That is, the direction of correction of the read depth and/or the magnitude of correction of the read depth may vary for each of the plurality of bins.

The correction data set 140 may be implemented and used in various formats such as a matrix, array, vector, etc. For example, in the form of a two-dimensional array, each row of the correction data set 140 represents one of the plurality of bins, and each column may represent a sample for each of the plurality of subjects based on the type of treatments (e.g., FFPE, FF) and/or the type of sample (e.g., normal cell sample, abnormal cell sample) used. The columns also represent the direction and/or the magnitude of correction of the read depth for each of the plurality of bins. A specific example of the correction data set 140 will be described in detail below in FIG. 4.

In the applying 160, the target sample data 150 may be corrected using the correction data set 140 and a first correction function 172. For example, the read depth associated with the target sample may be corrected by the first correction function 172 based on the information associated with the direction of correction and the information associated with the magnitude of correction included in the correction data set 140. This will be described below in detail with reference to FIGS. 5 and 6.

The noise in the first corrected data is removed using a second correction function 174 to generate corrected target sample data (FFPE X') 180. This will be described below in detail with reference to FIGS. 7 and 8.

Using the corrected target sample data 180 (e.g., corrected read depth), a copy number variation profile (CNV X') 190 associated with the target sample may be determined. For example, such determination may rely on the read depth associated with the normal cell sample in the target sample, the read depth associated with the abnormal cell sample in the target sample, and allele frequency associated with the target sample. At this time, the allele frequency depends on the purity (the ratio of abnormal cells in cells in the tissue being sequenced) and mean ploidy (average number of DNA in all regions, and for example, in normal human cells, DNA or genomes are present in pairs, so the mean ploidy corresponds to 2) of the target sample. The allele frequency is rarely influenced by the read depth. Therefore, compared to the read depth, the noise generated when measuring the allele frequencies for FFPE samples may not be considered a factor that can distort the analysis results.

The corrected read depth or the copy number variation profile determined using the corrected read depth may be added to the correction data set 140 and used again when correcting the read depth and determining the copy number variation profile for another subject.

Further, according to the embodiments provided in the present disclosure, a novel technique for determining a copy number variation profile is provided, by removing unnecessary noises. In these embodiments, convolution training time for neural networks can be reduced, and the accuracy of determination can be improved. For example, this novel technique can reduce the time taken by a neural network in achieving training the results of the determining the copy number variation profile by removing unnecessary noises. Further, for example, instead of using generalized or random filters, a novel technique of a specific filtering for removing unnecessary noises can be used, which lead to efficient and faster and accurate training of neural networks. This provides for fewer trials and errors. Further, this way, training may start off with lower learning rates and subsequently achieve convergence somewhat easily.

Figure 2:
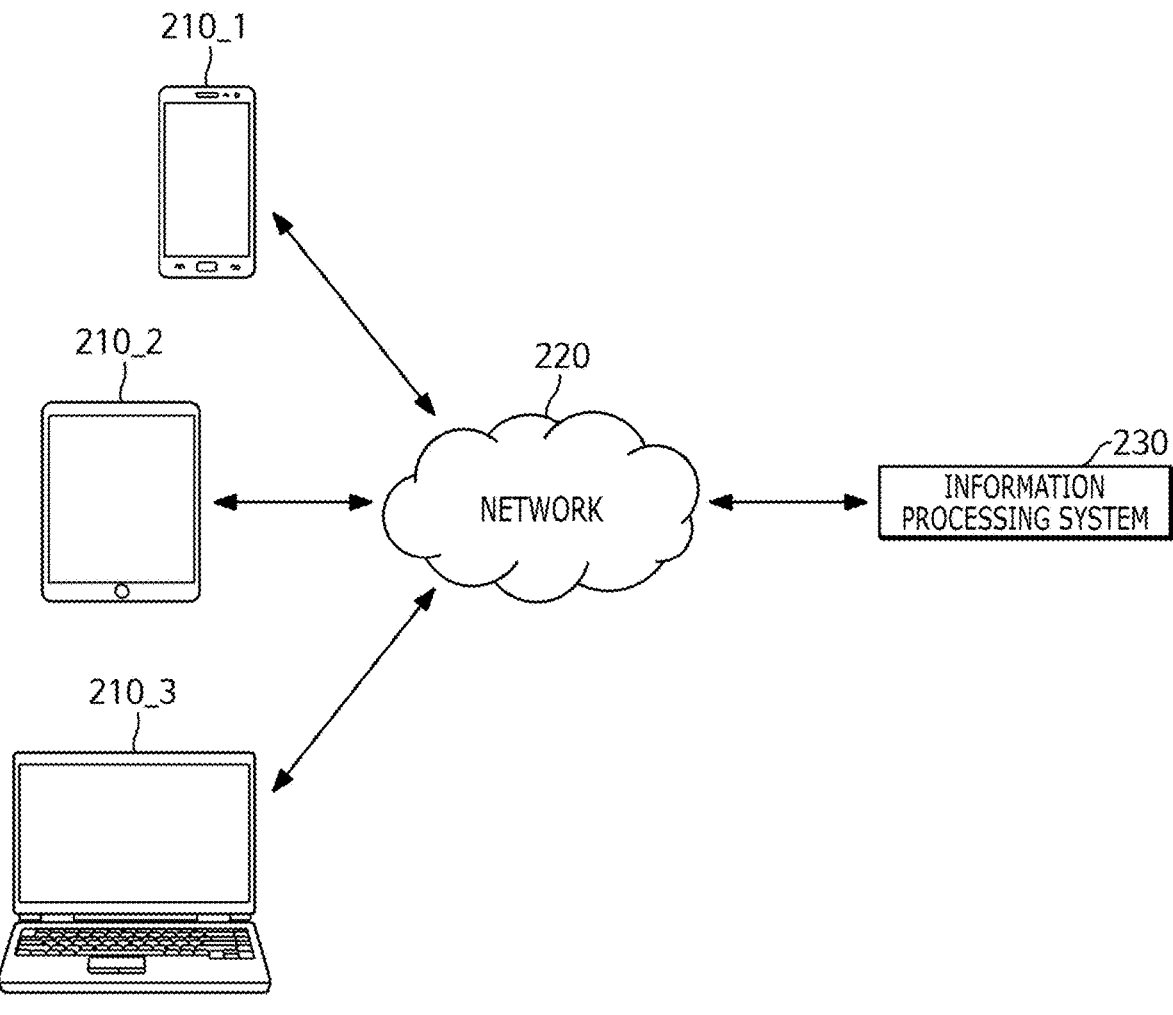
FIG. 2 is a schematic diagram illustrating a configuration in which an information processing system is communicatively connected to a plurality of user terminals in order to provide a service for determining a copy number variation profile.

FIG. 2 is a schematic diagram illustrating a configuration in which an information processing system 230 is communicatively connected to a plurality of user terminals 210_1, 210_2, and 210_3 to provide a service for determining a copy number variation profile. The information processing system 230 may include system(s) or computing device capable of providing a service for determining a copy number variation profile. The information processing system 230 may include one or more server devices and/or databases, or one or more distributed computing devices and/or distributed databases based on cloud computing services, which are capable of storing, serving, and executing computer-executable programs (e.g., downloadable applications) and data associated with a service for determining a copy number variation profile.

The service for determining a copy number variation profile provided by the information processing system 230 may be accessible to the users through an application or other software installed on each of the plurality of user terminals 210_1, 210_2, and 210_3.

The plurality of user terminals 210_1, 210_2, and 210_3 may communicate with the information processing system 230 through a network 220. The network 220 may be configured to enable communication between the plurality of user terminals 210_1, 210_2, and 210_3 and the information processing system 230. The network 220 may be configured as a wired network such as Ethernet, a wired home network (Power Line Communication), a telephone line communication device and RS-serial communication, a wireless network such as a mobile communication network, a wireless LAN (WLAN), Wi-Fi, Bluetooth, and ZigBee, or a combination thereof, depending on the installation environment. The method of communication is not limited, and may include a communication method using a communication network (e.g., mobile communication network, wired Internet, wireless Internet, broadcasting network, satellite network, etc.) that may be included in the network 220 as well as short-range wireless communication between the user terminals 210_1, 210_2, and 210_3.

For example, a plurality of user terminals 210_1, 210_2, and 210_3 may transmit a request to the information processing system 230 through the network 220, and the information processing system 230 may receive the request and transmit a response corresponding to the request to a plurality of user terminals 210_1, 210_2, and 210_3. For example, if a user terminal 210_1 transmits a request for results of whole-genome analysis and a request for copy number variation profile determination associated with the target sample to the information: processing system 230 (request), the information processing system 230 may transmit a copy number variation profile, etc. associated with the target sample to the user terminal 210_1 (response).

In FIG. 2, a mobile phone terminal 210_1, a tablet terminal 210_2, and a PC terminal 210_3 are illustrated as examples of user terminals, but aspects are not limited thereto, and the user terminals 210_1, 210_2, and 210_3 may be any computing device capable of wired and/or wireless communication and on which an application for determining a copy number variation profile, etc. can be installed and executed. For example, the user terminal may include a medical device, a smartphone, a mobile phone, a navigation system, a computer, a notebook computer, a digital broadcasting terminal, Personal Digital Assistants (PDA), a Portable Multimedia Player (PMP), a tablet PC, a game console, a wearable device, an internet of things (IoT) device, a virtual reality (VR) device, an augmented reality (AR) device, etc. In addition, FIG. 2 illustrates that three user terminals 210_1, 210_2, and 210_3 are in communication with the information processing system 230 through the network 220, but aspects are not limited thereto, and a different number of user terminals may be configured to be in communication with the information processing system 230 through the network 220.

FIG. 2 illustrates that the user terminal provides a copy number variation profile through network communication with the information processing system, but aspects are not limited thereto. Users may alternatively request the results of whole-genome analysis associated with a target sample and request determination of a copy number variation profile through an input device connected to the information processing system. Subsequently, the results of whole-genome analysis and the copy number variation profile associated with the target sample may be received through an output device connected to the information processing system.

Figure 3:
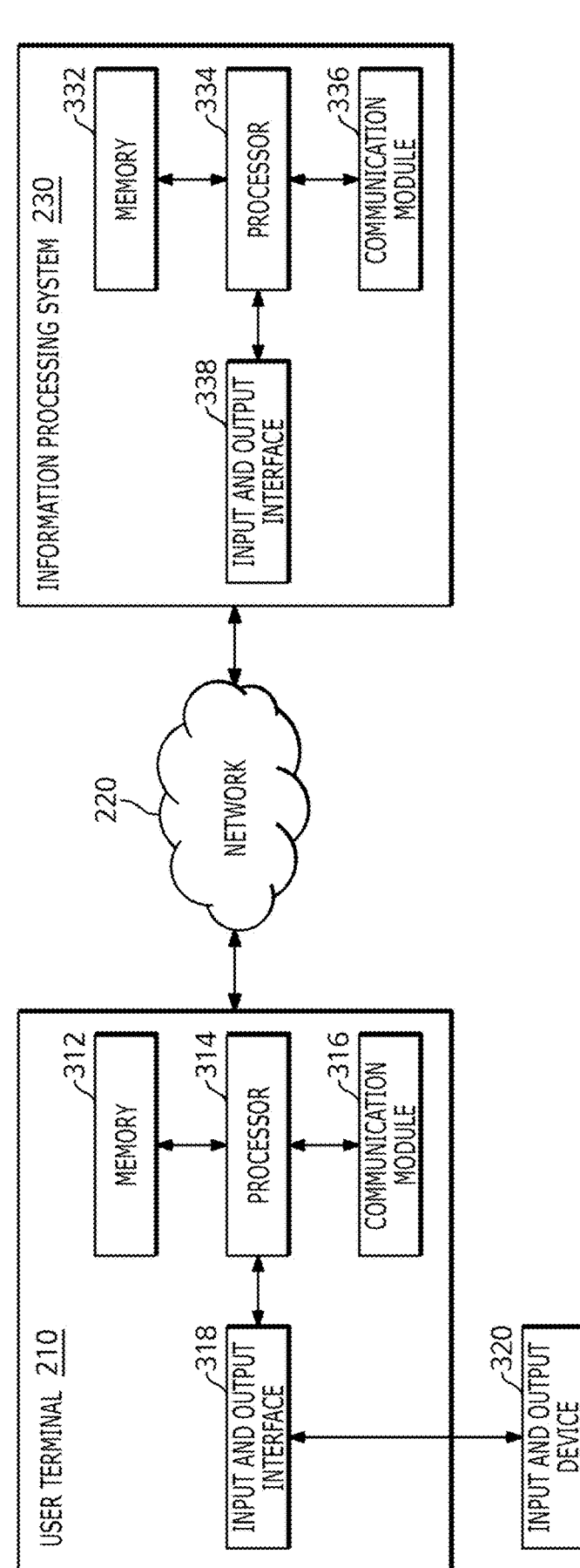
FIG. 3 is a block diagram of an internal configuration of the user terminal and the information processing system.

FIG. 3 is a block diagram of an internal configuration of a user terminal 210 and the information processing system 230. The user terminal 210 may refer to any computing device capable of executing an application for determining a copy number variation profile, among other functions, and supporting wired/wireless communication. Examples include the mobile phone terminal 210_1, the tablet terminal 210_2, the PC terminal 210_3 as depicted in FIG. 2. As illustrated, the user terminal 210 may include components such as a memory 312, a processor 314, a communication module 316, and an input and output interface 318. Similarly, (the information processing system 230 may include components including a memory 332, a processor 334, a communication module 336, and an input and output interface 338. As illustrated in FIG. 3, the user terminal 210 and the information processing system 230 may be configured to communicate information, data, etc. through the network 220 using the respective communication modules 316 and 336. In addition, the input and output device 320 may be configured to input information or data to the user terminal 210, or output information or data generated from the user terminal 210 through the input and output interface 318.

The memories 312 and 332 may include any computer-readable recording medium. The memories 312 and 332 may be any non-transitory computer-readable recording medium, and may include, for example, a permanent mass storage device such as read only memory (ROM), disk drive, solid state drive (SSD), flash memory, and others. As another example, a non-destructive mass storage device such as ROM, SSD, flash memory, disk drives, and the like may be included in the user terminal 210 or the information processing system 230 as a separate permanent storage device that is distinct from the memory. In addition, the memories 312 and 332 may store an operating system and at least one program code (e.g., code for an application for determining a copy number variation profile, etc.).

These software components may be loaded from a computer-readable recording medium separate from the memories 312 and 332. Such a separate computer-readable recording medium may include a recording medium directly connectable to the user terminal 210 and the information processing system 230, and may include a computer-readable recording medium such as a floppy drive, a disk, a tape, a DVD/CD-ROM drive, a memory card, and more. As another example, the software components may be loaded into the memories 312 and 332 through the communication modules 316 and 336 rather than from a separate computer-readable recording medium. For example, at least one program may be loaded into the memories 312 and 332 based on a computer program (e.g., an application for determining a copy number variation profile) installed by files provided through the network 220 by developers or a file distribution system that distributes application installation files.

The processors 314 and 334 may be configured to process the instructions of the computer program by performing basic arithmetic, logic, and input and output operations. The instructions may be provided to the processors 314 and 334 from the memories 312 and 332 or the communication modules 316 and 336. For example, the processors 314 and 334 may be configured to execute the received instructions according to a program code stored in a recording device such as the memories 312 and 332.

The communication modules 316 and 336 may provide a configuration or function for the user terminal 210 and the information processing system 230 to communicate with each other through the network 220, and may provide a configuration or function for the user terminal 210, the information processing system 230, etc. to communicate with another user terminal or another system (e.g., a separate cloud system, etc.). For example, the requests or data generated by the processor 314 of the user terminal 210 according to the program code stored in the recording device such as the memory 312 or the like may be transmitted to the information processing system 230 through the network 220 under the control of the communication module 316. Conversely, a control signal or command provided under the control of the processor 334 of the information processing system 230 may be received by the user terminal 210 through the communication module 316 of the user terminal 210 through the communication module 336 and the network 220.

The input and output interface 318 may be a means for interfacing with the input and output device 320. As an example, the input device may include a device such as a camera including an audio sensor and/or an image sensor, a keyboard, a microphone, a mouse, etc., and the output device may include a device such as a display, a speaker, a haptic feedback device, etc. As another example, the input and output interface 318 may be a means for interfacing with a device such as a touch screen, etc. that integrates a configuration or function for performing inputting and outputting. While FIG. 3 illustrates that the input and output device 320 is not included in the user terminal 210, aspects are not limited thereto, and the input and output device 320 may be configured as one device with the user terminal 210. In addition, the input and output interface 338 of the information processing system 230 may be a means for interfacing with a device (not illustrated) for inputting or outputting that may be connected to, or included in the information processing system 230. While FIG. 3 illustrates the input and output interfaces 318 and 338 as the components configured separately from the processors 314 and 334, aspects are not limited thereto, and the input and output interfaces 318 and 338 may be configured to be included in the processors 314 and 334.

The user terminal 210 and the information processing system 230 may include more components than the components illustrated in FIG. 3. Meanwhile, it would be unnecessary to exactly illustrate most of the related components. The user terminal 210 may be implemented to include at least a part of the input and output device 320 described above. In addition, the user terminal 210 may further include another component such as a transceiver, a global positioning system (GPS) module, a camera, various sensors, a database, etc.

The processor 314 of the user terminal 210 may be configured to run an application or a web browser application that provides a service for determining a copy number variation profile. In this case, a program code associated with the above application may be loaded into the memory 312 of the user terminal 210. While the application is running, the processor 314 of the user terminal 210 may receive information and/or data provided from the input and output device 320 through the input and output interface 318 or receive information and/or data from the information processing system 230 through the communication module 316, and process the received information and/or data and store it in the memory 312. In addition, such information and/or data may be provided to the information processing system 230 through the communication module 316.

While the application is running, the processor 314 may receive voice data, text, image, video, and the like input or selected through the input device such as a camera, a microphone, and the like that includes a touch screen, a keyboard, an audio sensor and/or an image sensor connected to the input and output interface 318, and store the received voice data, text, image, and/or video or the like in the memory 312, or provide it to the information processing system 230 through the communication module 316 and the network 220.

The processor 314 of the user terminal 210 may transmit and output the information and/or data to the input and output device 320 through the input and output interface 318. For example, the processor 314 of the user terminal 210 may output the processed information and/or data through the output device 320 such as a device capable of outputting a display (e.g., a touch screen, a display, and the like), a device capable of outputting a voice (e.g., speaker), etc.

The processor 334 of the information processing system 230 may be configured to manage, process, and/or store information, data, etc. received from a plurality of user terminals 210, a plurality of external systems, etc. The information and/or data processed by the processor 334 may be provided to the user terminals 210 through the communication module 336 and the network 220.

The processor 334 may calculate a read depth associated with the target sample for each of a plurality of predetermined bins on the genome, based on the results of whole-genome analysis associated with the target sample collected from the subject, correct the read depth associated with the target sample, and determine a copy number variation profile associated with the target sample using the corrected read depth. The determined copy number variation profile may be provided to the user terminal 210 through the communication module 336 and the network 220.

FIG. 4 illustrates an example of a correction data set 400. In FIG. 4, the correction data set 400 is illustrated in the form of a table, but this is for convenience of explanation and aspects are not limited thereto, and the correction data set 140 may be implemented and used in various formats such as matrix, array, vector, etc.

The correction data set 400 may be divided into two main areas: a first area 410 including data associated with each of a plurality of samples collected from a plurality of subjects different from the target subject, and a second area 420 including data for correcting the read depth associated with the target sample based on the data in the first area 410. Alternatively, the data in the first area 410 used for calculating the data in the second area 420 may not be included in the correction data set 400 or may be excluded from the correction data set 400.

In the correction data set 400, each row may represent one of a plurality of bins. Each of the plurality of bins, denoted as Bin 1 to Bin n, may be serve as a unit for grouping or classifying at least a portion of the genome for gene/genome analysis. The size of each of the plurality of bins may be chosen within the range of 100 kilobase pairs (kbps) to 1 megabase pairs (Mbps).

The division of the plurality of bins may be done in such a way that they do not share a common portion of the genome. For example, if each bin's size is 1 Mbps, Bin 1 may encompass the 1st to 1,000,000th bases on a specific chromosome, and Bin 2 may encompass 1,000,001 st to 2,000,000th bases on that chromosome. Alternatively, each bin may be divided in as way that they share a portion of the genome. For example, Bin 1 may encompass the 1st to 1,000,000th bases on a specific chromosome, and Bin 2 may encompass 500,001st to 1,500,000th bases on that chromosome. By employing this binning approach, where the genome is divided into a plurality of bins, the instability of the read depth of the target sample due to noise (whether random or non-random) when calculating the read depth can be significantly reduced.

The columns within the first area 410 correspond to samples of each of a plurality of subjects categorized by the treatment type (FFPE, FF). On the other hand, the columns within the second area 420 represent the direction of correction and/or magnitude of correction for the target object. The values within the correction data set 400 may represent the read depth for each of the plurality of bins in the first area 410, and may represent, in the second area 420, the direction of correction, magnitude of correction, and correction coefficient for application (adjustment) to the read depth for each of the plurality of bins. For example, "Depth_111" illustrated in FIG. 4 may represent the read depth for the first bin calculated from a sample (either a normal cell sample or an abnormal cell sample) obtained from a particular subject and processed by FFPE treatment method. In this case, the read depth of each of the plurality of bins (any one of Depth_111 to Depth_2$mn$) may be a representative value of the plurality of read depths for each of the plurality of bins (that is, the read depth for the plurality of reads classified into each of the plurality of bins), and may correspond to the arithmetic mean or median of a plurality of read depths.

The information associated with the direction of correction may be determined based on a distribution p of read depths associated with all FFPE samples in the data set for each of the plurality of bins, and a distribution q of read depths associated with all FF samples in the data set for each of the plurality of bins. For example, the information associated with the direction of correction for Bin 1 may be determined based on a distribution of Depth_111 to Depth_11$n$ and a distribution of Depth_211 to Depth_21$n$.

For example, if there is a meaningful difference between the distributions p and q for the corresponding bin (that is, if there is a meaningful difference between the mean and median, etc. of the two distributions even after considering randomness) as a result of a test (e.g., Student's t-test based on p-value 0.05) to determine whether there is a statistically meaningful difference between the distributions p and q, the corresponding bin is determined to be an area where noise occurs, and information associated with the direction of correction for the corresponding bin may be set to "1" or "−1". Conversely, if no meaningful difference is observed between the distributions p and q, the information associated with the direction of correction for the bin in question may be set to "0".

If the read depth associated with all FFPE samples (or the mean or median of distribution p, etc.) is determined to be statistically greater than the read depth associated with all FF samples (or the mean or median value of the distribution q, etc.) based on the distributions p and q, the information associated with the direction of correction for the corresponding bin may be set to "−1"; otherwise, it may be set to "1".

A value of "−1" in the information associated with the direction of correction for a specific bin may indicate that the read depth for the corresponding bin should be corrected in the decreasing (−) direction, while a value of "1" may indicate that the read depth should be corrected in the increasing (+) direction. A value of "0" may indicate that the read depth correction is unnecessary. Referring to FIG. 4, for example, the read depth of the target sample for Bin 1 may indicate that the read depth should be corrected in the decreasing direction, while the read depth of the target sample for Bin n may indicate that the read depth should be corrected in the increasing direction. On the other hand, the read depth of the target sample for Bin 2 may indicate that the read depth does not need to be corrected.

The information associated with the magnitude of correction may be determined based on an average of read depths associated with all FFPE samples in the data set for each of the plurality of bins, and an average of read depths associated with all FF samples in the data set for each of the plurality of bins. For example, the information associated with the magnitude of correction for Bin 1 may be an absolute value of the difference between the average of Depth_111 to Depth_11n and the average of Depth_211 to Depth_21n.

The correction coefficient for adjusting the read depth may be determined by multiplying the direction of correction by the magnitude of correction. The correction coefficient determined for each of the plurality of bins may be used for correcting the read depth associated with the target sample for each of the plurality of bins. This will be described below in detail with reference to FIGS. 5 and 6.

Figure 5:
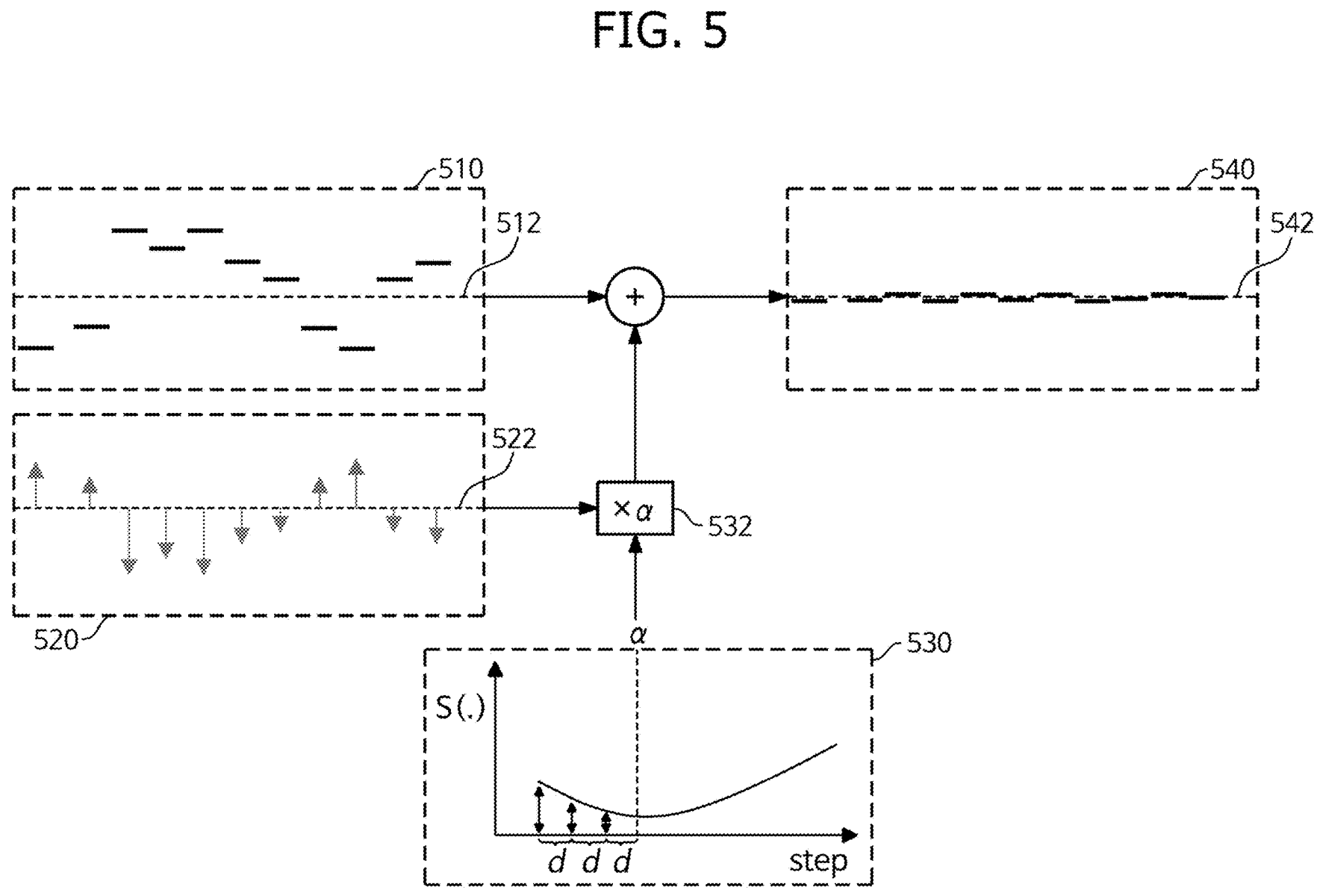
Figure 6:
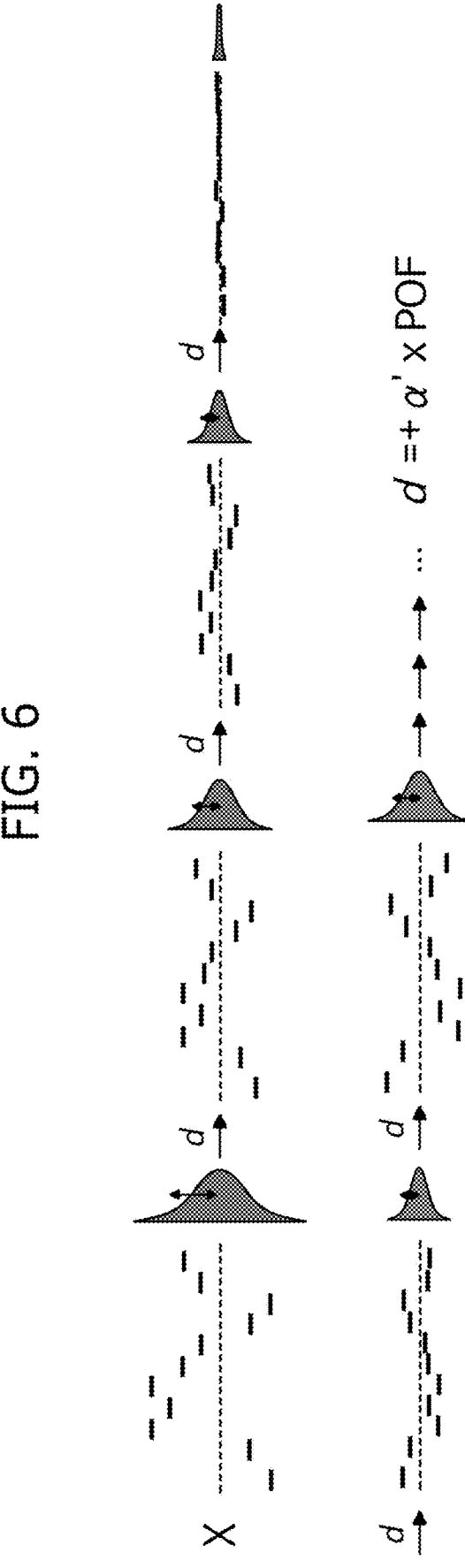
FIG. 6 illustrates a process of determining a value of a correction variable that minimizes the outcome of a standard deviation function.

FIG. 5 illustrates a first correction process of a read depth associated with a target sample for each of a plurality of bins, and FIG. 6 illustrates a process of determining a value of a correction variable 532 that minimizes the result of a standard deviation function. For the first correction process, a plurality of bins ("primary bins") may be grouped into a plurality of larger bins ("secondary bins", "bin-of-bin", or "sub-bins"). For example, for a subject's-genome comprising approximately 3 billion base pairs, around 30,000 primary bins may be identified, each encompassing 100,000 bases. Subsequently these 30,000 primary bins may be grouped into about 100 secondary bins, each encompassing about 300 primary bins. The number of secondary bins may range from 50 to 150, but aspects are not limited thereto.

As illustrated in FIG. 5, read depth data 510 for the secondary bin may include read depths (represented by horizontal bars arranged above or below a first reference line 512) for each of the plurality of primary bins. The first reference line 512 may serve as a baseline for the true read depth associated with each of the primary bins in relation to the target sample or the read depth calculated from the FF target sample. The distance by which the read depth for each of the plurality of primary bins diverges from the first reference line 512 may represent the difference from the read depth determined using the true ground data or the FF target sample.

Correction coefficient data 520 may include a plurality of correction coefficients for correcting the read depth for the primary bin. A second reference line 522 represents a correction coefficient of 0, and the arrows representing the correction coefficient may represent the direction of correction and magnitude of correction of the read depth for each of the plurality of primary bins. The correction coefficient may correspond to a fixed value regardless of the type of target sample, extraction target, etc.

Read depth data associated with the target sample for each of a plurality of bins (primary bins) may be first corrected by Equations 1 and 2 below.

$$X'_{i\,RDR} = X_{i\,RDR} + \alpha \times POF_{i,adjust} \text{ where } \alpha \in [0, \infty) \qquad \text{<Equation 1>}$$

$$\alpha = \arg\min_{\alpha'} s(X_{iRDR} + POF_{i,adjust}) \qquad \text{<Equation 2>}$$

where, $X'_{iRDR}$ may be first corrected read depth data 540 for the i-th secondary bin, $X_{iRDR}$ may be the read depth data 510 before first correction for the secondary bin, $POF_{i,adjust}$ may be the correction coefficient, $\alpha$ may be the correction variable 532, and s( ) may be a standard deviation function 530. That is, the correction variable (a) 532 may be determined based on any variable value ($\alpha'$) that minimizes the standard deviation calculated by multiplying any variable value ($\alpha'$) by the correction coefficient and then adding the read depth data for each of the primary bins included in the secondary bin. The read depth data for each of the primary bins included in the secondary bin may be first corrected by adding a correction constant, which is the outcome of multiplying the correction coefficient (a constant value) by a specific correction variable ($\alpha$) 532 tailored to the target sample. That is, the correction constant, utilized for the first correction of the read depth data for each of the primary bins, may be calculated by the product of a fixed correction coefficient and a target-sample-specific correction variable.

A single correction variable ($\alpha$) 532 may be determined for a plurality of primary bins contained within a secondary bin, and the determined correction variable ($\alpha$) 532 may be used for the read depth data for each of the plurality of primary bins. That is, each of the secondary bins may not overlap with other secondary bins, leading to the determination of a single correction constant for a specific primary bin. Conversely, secondary bins may overlap with each other, including primary bins shared with other secondary bins, resulting in the determination of more than one correction constants for a single primary bin. In such cases, the final correction constant may be determined by taking the average value, median value, or another appropriate statistic from the one or more determined correction constants.

Since the standard deviation function 530 behaves as a convex function with respect to the correction variable ($\alpha'$), it always exhibits a unique minimum value. Accordingly, the correction variable ($\alpha$) 532 may be determined as a single variable value using methods such as a grid search, line search, and others. For example, as illustrated in FIG. 6, the standard deviation may be calculated by repeatedly adding d to the read depth for each of the primary bins. FIG. 6 illustrates that the standard deviation initially decreases and then increases, with the minimum value achieved when d is added for the third time. Accordingly, the value of the correction variable ($\alpha$) 532 may be determined as $\alpha=3d$.

In summary, the first correction process uses a pattern of increasing and decreasing the read depth by the similar degree across a plurality of samples. The first correction process may correspond to a method of correcting the read depth values by decreasing the calculated read depth if it surpasses the standard, or increasing the calculated read depth if it falls below the standard. Such patterns of read depth increase or decrease are not restricted to specific samples but are universally identified. Multiple lines of direct and indirect evidence support the existence of such patterns. For example, depending on the GC-richness of each sample, the double bond strength and charge distribution of the DNA in each sample is different, and the degree to which the DNA tries to maintain its structure in each sample is different. In addition, DNA exists as a three-dimensional structure wound like a thread around nucleosomes, and the three-dimensional structure is different depending on the epigenetic modification of DNA or nucleosomes. As a result, the DNA of each sample differs not only in its internal properties but also in its resistance to external changes. In FFPE processed samples, DNA cross-linking is known to occur due to the solutions used to preserve the tissue, and the areas that are more or less prone to cross-linking can be significantly influenced by the above factors.

As an alternative to the example illustrated and described in FIGS. 5 and 6, the read depth data may be corrected by excluding read depth data from regions where the distribution of read depth exhibits excessive increase or decrease over a specific narrow range (i.e., where the change in read depth distribution within the region is equal to or greater than a threshold).

Figure 7:
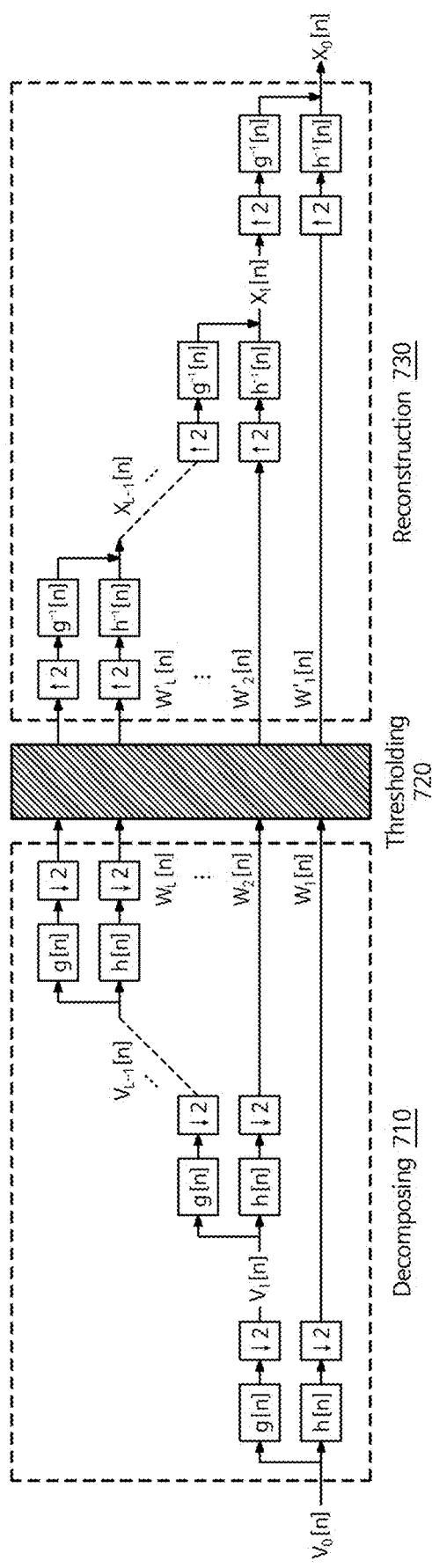
FIG. 7 illustrates a process in which second correction is performed to remove noise from the read depth, subsequent to the first correction.
Figure 8:
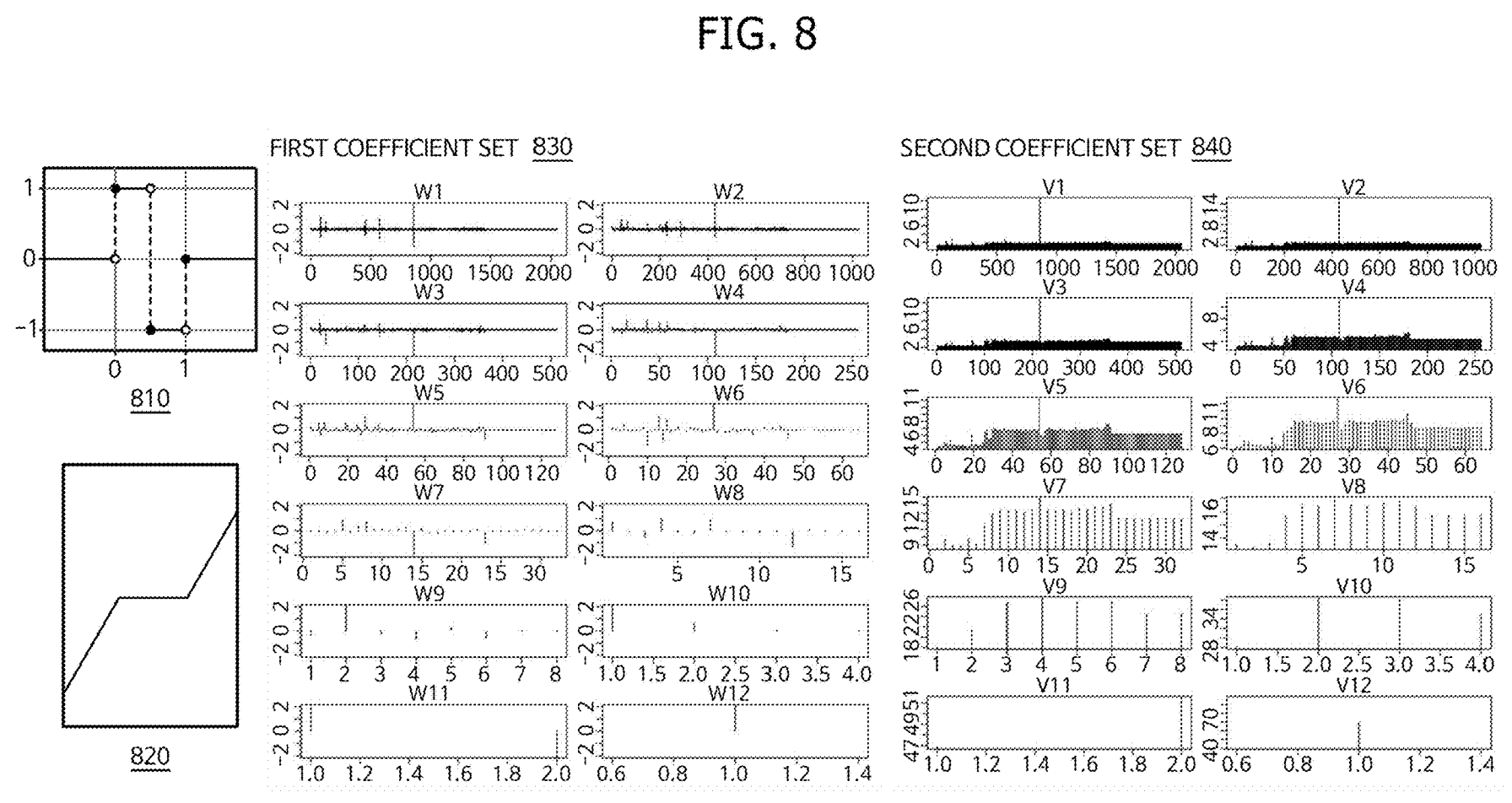

FIG. 7 illustrates a process in which second correction is performed to remove noise from the read depth data following the first correction. FIG. 8 illustrates examples of graphs 810 and 820, alongside coefficient sets 830 and 840, which are used during the second correction. The second correction is the process of removing noise from data. The second correction may correspond to the process of removing random fluctuations in read depth occurring at a local level. It is performed subsequent to the first correction process, which corrects the macroscopic fluctuations in read depth at a larger scale within the FFPE sample. The second correction process may include decomposing 710, thresholding 720, and reconstruction 730. The second correction process may be applied either across the entire genome or to specific genomic segments, such as individual chromosomes.

In the decomposing 710, level L at which the coefficient set will be calculated may be set. The maximum value of L, denoted as $L_{max}$, may be determined as $\log_2(N)$ according to the length of the input data or the number N of secondary bins, and the level may be a natural number between 1 and $L_{max}$.

In the decomposing 710, the first corrected data may assume the form of a one-dimensional vector. For example, the first corrected read depth for a plurality of bins may be expressed and processed as a one-dimensional vector.

When the data length N is not a multiple of 2, zero padding may be added to the data such that the data length N is the smallest multiple of 2 that is greater than N. For example, in the case of read depth data for each of 3,000 bins, 1096 zero paddings may be appended, and $L_{max}$ may be determined as $\log_2(4096)=12$. Through this approach, the data may undergo sequential downsampling to ½ of its original size in the decomposing 710.

By applying a wavelet function (wavelet function 810 in FIG. 8) to the data at each of the levels i=1, ..., $L_{max}$, two sets of coefficients are determined. The first coefficient set 830 may include detailed wavelet coefficient $W_i$. The second coefficient set 840 may include approximate wavelet coefficient $V_i$.

The process of determining the detailed wavelet coefficient and the approximate wavelet coefficient is expressed in Equation 3 below.

$$y_{i+1}[n] = \qquad\qquad\qquad\qquad\qquad\qquad \text{<Equation 3>}$$

$$(y_i * f)[n] = \sum\nolimits_{k=-\infty}^{\infty} y_i[k]\, f[2n - k] \text{ where } i = 0, 1, \dots, L.$$

In Equation 3, n refers to the index of the data and may have an integer value from 0 to N−1. When i=0, $y_0$ ($V_0[n]$ in FIG. 7) may be input data (e.g., first corrected read depth data for each of a plurality of bins) of the decomposing 710. f[n] may be determined by selecting from various wavelets such as Haar, Daubechies, Coiflet, Best-localized Daubechies, or Least asymmetric wavelet. f[n] may be selected as the Haar wavelet function 810 of FIG. 8, which is known to be most suitable for application to data in the form of a step function (e.g., copy number variation profile or read depth profile) with discrete values. The Haar wavelet function 810 may be transformed and expressed as a high-pass filter (HPF) h[n] and a low-pass filter (LPF) g[n] according to Equation 4 below. That is, in Equation 3, f[n] may be h[n] using the high-pass filter, and may be g[n] using the low-pass filter.

$$h[n] = \frac{1}{\sqrt{2}} 1_0(n) - \frac{1}{\sqrt{2}} 1_1(n),\ g[n] = \frac{1}{\sqrt{2}} 1_0(n) + \frac{1}{\sqrt{2}} 1_1(n) \quad \text{<Equation 4>}$$

where, $1_x(n)$ is an indicator function, and corresponds to a function that has a value of 1 only in n=x and has 0 in the remaining areas. The high-pass filter may capture local data features by passing frequencies above a certain cutoff frequency and attenuating frequencies below it, and conversely, the low-pass filter may capture macroscopic data features by attenuating frequencies above a certain cutoff frequency and passing frequencies below it.

Back to Equation 3, $y_i$ of the input part may be $V_0[n]$ of FIG. 7 or $V_i[n]$ that passes through the low-pass filter g(n) and is downsampled by ½ (where i=1, 2, ..., L−1). $y_i*f$ may represent a function in which the result of convolution of $V_i[n]$ passed through the low-pass filter and downsampled by ½ (where i=1, 2, ..., L−1), and the low-pass filter or the high-pass filter is downsampled to ½. The output value $y_{i+1}[n]$ may correspond to the approximate wavelet coefficient $V_i$ of FIG. 7 (where i=1, 2, ..., L) when passing through the low-pass filter, and may correspond to the detailed wavelet coefficient $W_i$ of FIG. 7 (where i=1, 2, ..., L) when passing through the high-pass filter.

In the thresholding 720, the detailed wavelet coefficients determined in the decomposing 710 may be subject to thresholding.

Soft-thresholding may be applied to the detailed wavelet coefficients. For example, the detailed wavelet coefficients whose absolute values fall below a certain threshold are set to 0. When the absolute values exceed the threshold, detailed wavelet coefficients are significantly reduced as they approach the threshold. In other words, soft-thresholding allows for the attenuation of the detailed wavelet coefficient as their absolute values approach the threshold because they contain a certain degree of noise even if their absolute values exceed the threshold. During soft-thresholding, the detailed wavelet coefficients $W_i$ with $|W_i|$ less than the threshold may be replaced with 0 by the soft-thresholding function 820, while other areas may be scaled linearly.

Additionally, or alternatively, hierarchical thresholding of the detailed wavelet coefficients may be performed. As the level i increases from 1 to $L_{max}$, the threshold $\lambda$ value may decrease. Through this approach, the higher-level detailed wavelet coefficients, which contain information about the macroscopic shape of the signal, are less likely to be set to zero or attenuated. This preserves the macroscopic copy number variation profile as much as possible. That is, a high-frequency noise can be specifically removed through hierarchical thresholding. For example, the threshold $\lambda$ may be weighted with a value of $1-\alpha*i$ for level i, as illustrated in Equation 5 below.

$$\lambda = \sqrt{2\sigma\log N} * (1 - \alpha * i) \qquad \text{<Equation 5>}$$

where, N is the data length or the total number of secondary bins, $\alpha$ is any predetermined constant and its value may be adjusted later. For example, if it is determined that noise removal from the read depth correction is insufficient, the $\alpha$ value may be reduced to increase the threshold, resulting in more effective noise removal. The $\sigma$ value may be estimated using the mean absolute deviation (MAD) as shown in Equation 6 below.

$$\sigma = \frac{\text{median}(|W_i|)}{0.6745} \qquad \text{<Equation 6>}$$

In the reconstruction 730, the reverse of the decomposing 710 may be performed. For example, the thresholded detailed wavelet coefficients and their corresponding approximate wavelet coefficients may be alternately arranged and upsampled. Sequential convolution of g[−n] and h[−n] may be performed for each level as described in Equation 4 for functions g and h.

As aforementioned, the above novel technique of removing unnecessary noises may achieve technical improvement of reducing the overall data size, increasing accuracy of determining correct profile, and increasing speed of determined profile.

Figure 9:
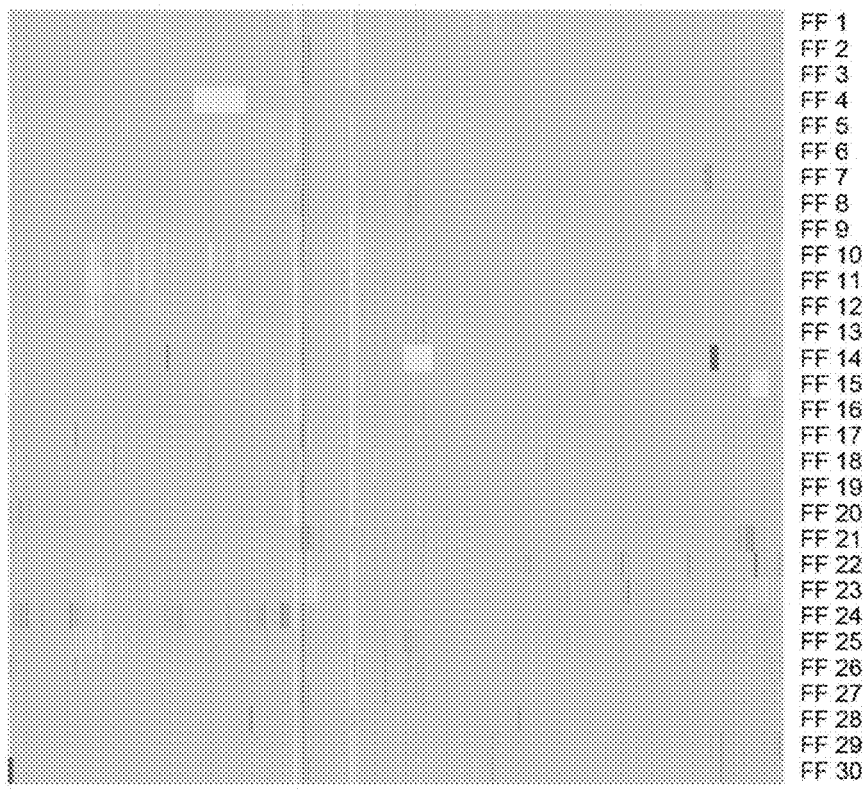
FIG. 9 illustrates an example of a first heat map associated with an FF sample and a second heat map associated with an FFPE sample.
Figure 9:
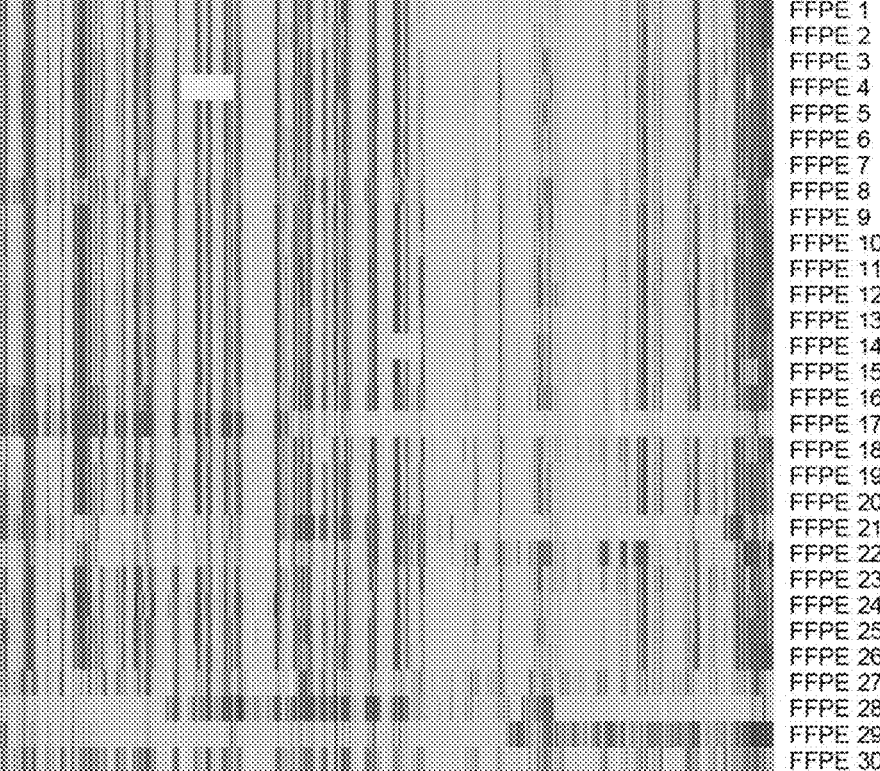

FIG. 9 illustrates an example of a first heat map 910 associated with an FF sample and a second heat map 920 associated with an FFPE sample. The indices along the vertical axis in FIG. 9 may represent samples collected from different subjects, where samples with are collected from the same subject. For example, "FF 1" of the first heat map 910 and "FFPE 1" of the second heat map 920 represent samples from the same subject treated with different methods.

The second heat map 920 exhibits a striped pattern, while the first heat map 910 does not. The striped pattern in the second heat map 920 represents specific noise generated in the FFPE samples, where the read depth changes (either increases or decreases) to a similar extent at each position among the plurality of FFPE samples.

Figure 10:
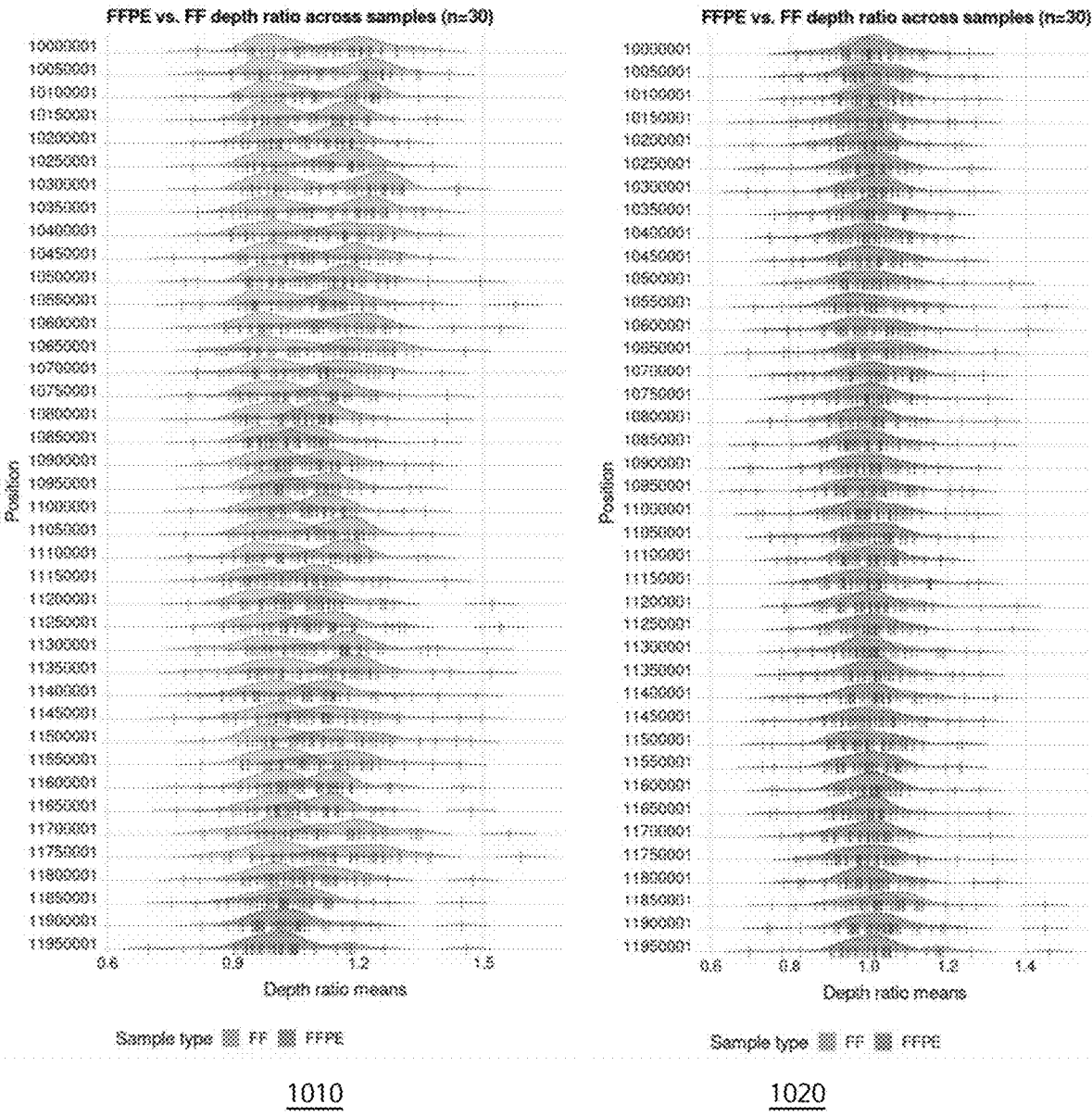
FIG. 10 illustrates examples of distribution graphs depicting the read depth ratios for each sample, both prior to and following the correction of the read depth associated with an FFPE sample.

FIG. 10 illustrates examples of distribution graphs 1010 and 1020 showing read depth ratios for each sample before and after the correction of the read depth associated with the FFPE samples. The first graph 1010 shows the distribution of average read depth ratios for each sample before the correction, while the second graph 1020 shows the distribution of average read depth ratios for each sample after correction of the read depth associated with the FFPE samples. The indices indicated along the vertical axis of the graphs 1010 and 1020 correspond to specific positions in the genomic base sequence.

In the first graph 1010, it can be seen that the read depth ratios follow different distributions depending on the sample treatment methods (e.g., FFPE, FF). On the other hand, in the second graph 1020, the read depth associated with the FFPE sample has been corrected, resulting in a similar distribution patterns for read depth ratios across sample treatment methods. This demonstrates that by applying the read depth correction method according to the present disclosure, similar data can be obtained for determining the copy number variation profiles (or read depth) when using FFPE samples as compared to using FF samples.

Figure 11:
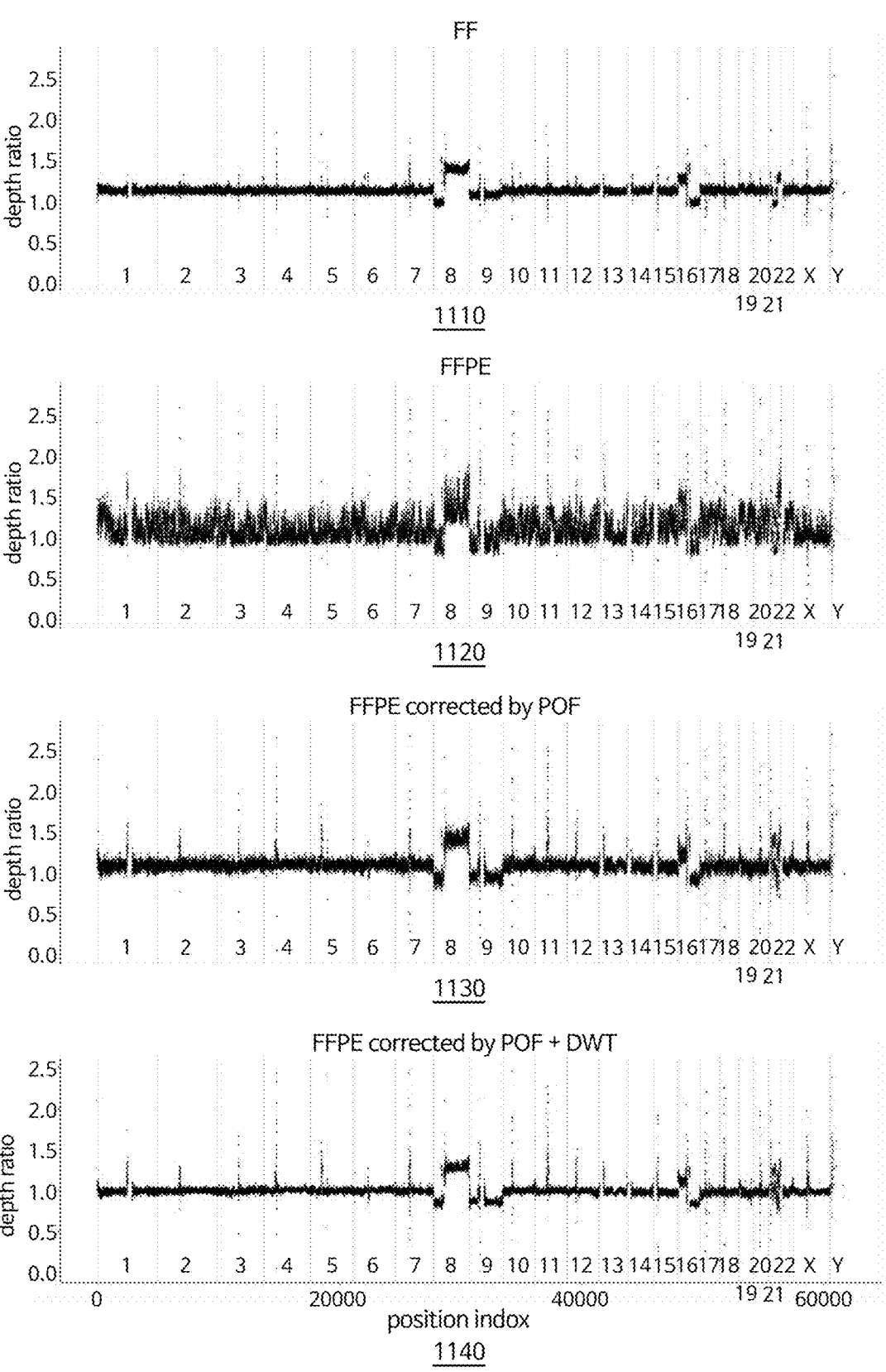
FIG. 11 illustrates examples of the distribution patterns of read depths across each of chromosomes.

FIG. 11 illustrates examples of the distribution of read depth for each chromosome. The indices along the horizontal axis of each of the graphs 1110, 1120, 1130, and 1140 represent autosome numbers and sex chromosomes, while the indices along the vertical axis represent the read depth ratio. The black dots in each of the graphs 1110, 1120, 1130, and 1140 may represent the ratio, in terms of bins, between the read depth obtained from sequencing a normal cell sample and the read depth obtained from sequencing an abnormal cell sample, at a specific positions on a base sequence.

The first graph 1110 shows the distribution of read depth obtained from FF samples, the second graph 1120 shows the distribution of read depth obtained from FFPE samples from the same subject, the third graph 1130 shows the distribution of read depth obtained from the FFPE sample after applying the first correction process according to the present disclosure, and the fourth graph 1140 shows the distribution of read obtained from the FFPE sample after applying both the first correction process and the second correction process according to the present disclosure.

It can be seen that the distributions in the first graph 1110 and the second graph 1120 exhibit some differences, with the second graph 1120 displaying high frequency noise. On the other hand, the third graph 1130 reveals a correction of data, rendering it similar to the distribution in the first graph 1110. Furthermore, the fourth graph 1140, where additional noise is removed from the data of the third graph 1130, the distribution closely resembles that in the first graph 1110.

Figure 12:
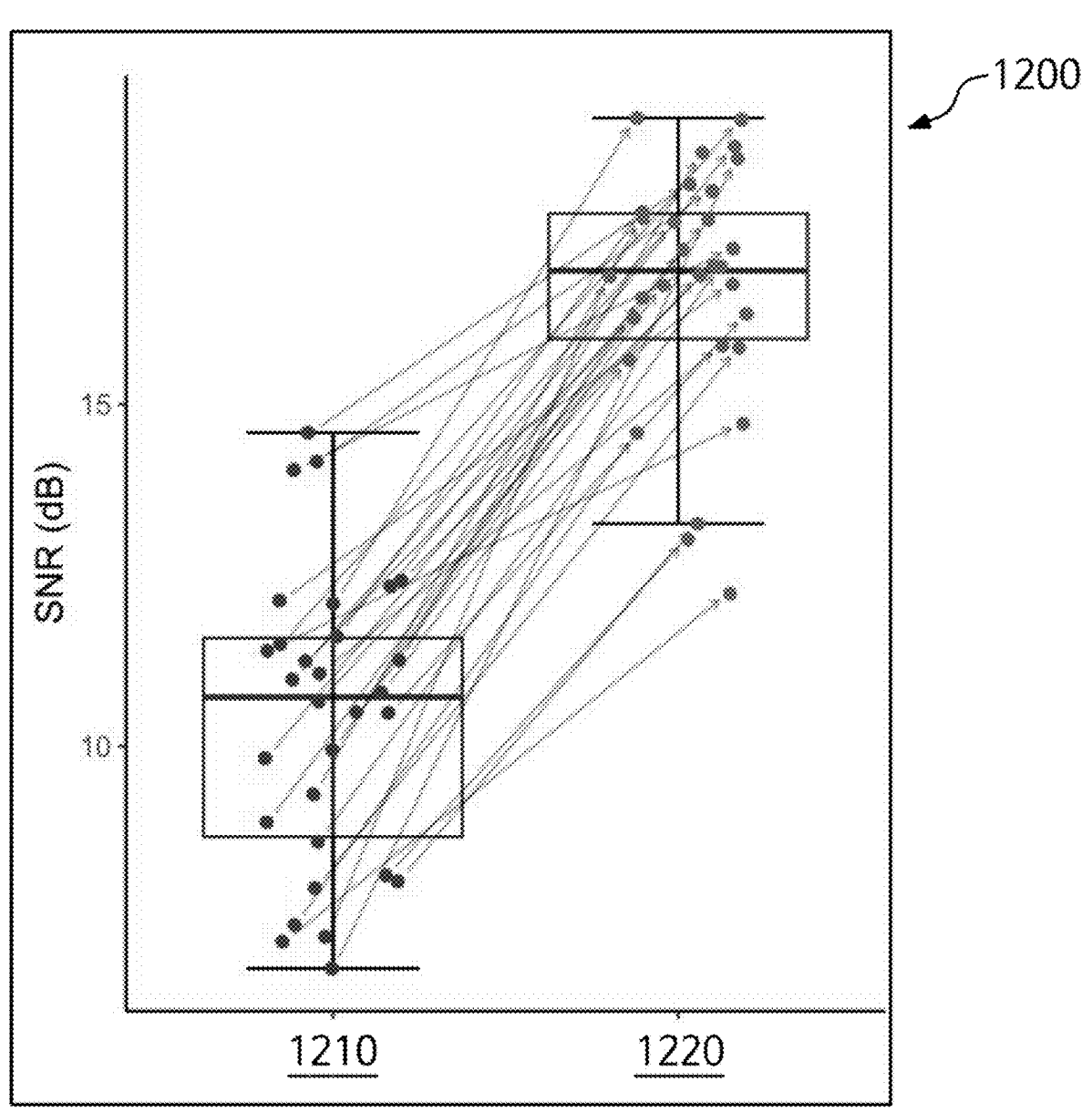
FIG. 12 illustrates an SNR (Signal-to-Noise Ratio) graph for evaluating the degree of qualitative improvement in the copy number variation profile according to read depth correction.

FIG. 12 illustrates a signal-to-noise ratio (SNR) graph 1200 for evaluating the degree of qualitative improvement in the copy number variation profile according to read depth correction. The SNR value may be calculated for each sample (indicated by a dot), and the SNR graph 1200 illustrated in FIG. 12 includes a first box plot 1220 showing the SNR value calculated before the correction of the read depth for each sample and a second box plot 1220 showing the SNR value calculated after the correction of the read depth of the FFPE sample. The SNR value may be calculated by the following Equation 7.

$$SNR = 10\log_{10}\left(\frac{E[D_{FF}]}{\text{Var}(D_{FF} - D_{FFPE})}\right) \qquad \text{<Equation 7>}$$

where, $D_{FF}$ is obtained by interpreting the read depth of the FF sample as a random variable, and $D_{FFPE}$ is obtained by interpreting the read depth of the FFPE sample as a random variable.

According to the present disclosure, when correction is made only to the read depth of the FFPE sample, $D_{FF}$ may be the same before and after the correction of the read depth, and $D_{FFPE}$ may differ before and after the correction of the read depth. As a result, it can be seen that the SNR value in a first box plot 1210 increases overall in the second box plot 1220 after the correction of the read depth. That is, it can be seen that the quality of the copy number variation profile is improved by the correction of the read depth.

FIG. 13 is a flowchart illustrating a method 1300 for determining a copy number variation profile. The method 1300 may be performed by one or more processors (e.g., a processor of a user terminal, a processor of an information processing system, or a processor of an apparatus for determining a copy number variation profile, etc.). The method 1300 may be initiated by the processor acquiring results of whole-genome analysis associated with a target sample collected from the subject, at S1310. The target sample may be a formalin-fixed, paraffin-embedded (FFPE) sample.

The processor may calculate a read depth associated with the target sample for each of a plurality of predetermined bins on the genome, based on the acquired results of whole-genome analysis, at S1320.

The processor may correct the read depth associated with the target sample, at S1330.

The processor may perform a first correction of the read depth associated with the target sample using a data set including read depth data for each of the plurality of bins associated with each of a plurality of samples collected from a plurality of subjects different from the subject. In this case, the data set may include at least one of data associated with a normal cell sample collected from each of the plurality of subjects or data associated with an abnormal cell sample collected from each of the plurality of subjects, and each of the normal cell sample collected from each of the plurality of subjects and the abnormal cell sample collected from each of the plurality of subjects may include an FFPE sample and a fresh frozen (FF) sample.

The data set may further include information associated with a direction of correction of read depth for each of the plurality of bins, for use in correcting the read depth of the target sample. The information associated with the direction of correction of the read depth for each of the plurality of bins may be determined based on a distribution of read depths associated with all FFPE samples in the data set for each of the plurality of bins and a distribution of read depths associated with all FF samples in the data set for each of the plurality of bins.

The data set may further include information associated with a magnitude of correction of read depth for each of the plurality of bins, for use in correcting the read depth of the target sample. The information associated with the magnitude of correction may be determined based on an average of read depths associated with all FFPE samples in the data set for each of the plurality of bins and an average of read depths associated with all FF samples in the data set for each of the plurality of bins.

The processor may perform the first correction by correcting the read depth associated with the target sample based on the information associated with the direction of correction and the information associated with the magnitude of correction.

The processor may further perform the second correction to remove noise from the first corrected read depth. The processor may determine a plurality of wavelet coefficients using a predetermined wavelet and the first corrected read depth, and may threshold a plurality of wavelet coefficients and determine a second corrected read depth based on the plurality of thresholded wavelet coefficients. At this time, the predetermined wavelet may correspond to the Haar wavelet.

If the absolute value of a specific wavelet coefficient of a plurality of wavelet coefficients is less than a predetermined threshold, the processor replaces the specific wavelet coefficient with 0, and if the absolute value of the specific wavelet coefficient is equal to or greater than the threshold, the processor may attenuate specific wavelet coefficients to a higher degree as the difference between the absolute value and the threshold decreases, thereby thresholding a plurality of wavelet coefficients. The threshold may be lower as the specific wavelet coefficients are higher-level wavelet coefficients.

The processor may determine a copy number variation profile associated with the target sample using the corrected read depth, at S1340. The target sample may include a normal cell sample and an abnormal cell sample collected from the subject, and the processor may determine the copy number variation profile based on the read depth associated with the normal cell sample, the read depth associated with the abnormal cell sample, and the allele frequency associated with the target sample.

The flowchart illustrated in FIG. 13 and the above description are merely examples and may be implemented differently in some examples. For example, one or more operations may be omitted, the order of operations may be changed, one or more operations may be performed in parallel, or one or more operations may be repeatedly performed multiple times.

Further, one or more practical applications can be provided by using the copy number variation profile.

In some embodiments, driver genes can be identified. The copy number variation profile can help identify driver genes, which are genes that are directly involved in cancer development and progression. The amplification (gain) of specific genes due to the copy number variation profiles can lead to overexpression of oncogenes, which promote tumor growth. Conversely, the deletion (loss) of tumor suppressor genes due to the copy number variation profiles can lead to the loss of their protective functions against cancer.

In some embodiments, prognosis and predicting clinical outcomes can be provided by using the copy number variation profile. The copy number variation profiles can provide valuable prognostic information. For instance, certain copy number variation profiles may be associated with chromosomal instability and indicative of a more aggressive cancer phenotype and worse clinical outcomes. By analyzing copy number variation profiles, clinicians can predict patient survival, response to therapy, and disease progression.

In some embodiments, disease progression can be monitored by using the copy number variation profile. The copy number variation profiles can be monitored over time to assess disease progression and response to treatment. Changes in copy number variation profiles can indicate the development of treatment resistance or the emergence of new genetic alterations that may require different therapeutic approaches.

In some embodiments, research and drug development can be performed by using the copy number variation profile. The copy number variation profile data is essential for cancer research and drug development. Researchers use copy number variation profile information to better understand the underlying genetic mechanisms driving cancer and to identify potential drug targets. It also helps in developing preclinical models for testing new therapies.

In some embodiments, early detection can be performed by using the copy number variation profile. The copy number variation profiles can sometimes be detected in early-stage cancer, even before clinical symptoms manifest. This early detection can aid in cancer screening and diagnosis, potentially leading to more effective treatment outcomes.

In some embodiments, a method for determining a copy number variation profile by using read depth correction, being executed by one or more processors, performs: collecting, by using a medical device, a target sample from a subject; performing, by using a hardware processor of a server device, a whole-genome analysis for the target sample; acquiring, by a client device, results of the whole-genome analysis associated with the target sample; calculating, by the client device, a read depth associated with the target sample for each of a plurality of predetermined bins on genome based on the acquired results of whole-genome analysis; correcting, by the client device, the read depth associated with the target sample; determining, by the client device, a copy number variation profile associated with the target sample using the corrected read depth; storing, by the client device, the determined copy number variation profile associated with the target sample in memory; performing, by the client device, a machine learning on the stored copy number variation profile by using a neural network; identifying, by the client device, driver genes, which are directly involved in cancer development and progression, by analyzing the copy number variation profile, and transmitting information on the identified driver genes to a user device; and monitoring, by the client device, the cancer development and progression by monitoring changes in the copy number variation profile.

Accordingly, the copy number variation profile of the cancer sample is very important for providing the identification of the driver genes and the monitor of the cancer development and progression. In this situation, most of the samples available in clinical practice are. FFPE, and the quality of the copy number variation profile can be poor. Thus, the novel way of removing noises in the samples has the great technical significance to obtain the profile with high accuracy and speed, without using huge resources.

The method described above may be provided as a computer program stored in a computer-readable recording medium for execution on a computer. The medium may be a type of medium that continuously stores a program executable by a computer, or temporarily stores the program for execution or download. In addition, the medium may be a variety of writing means or storage means having a single piece of hardware or a combination of several pieces of hardware, and is not limited to a medium that is directly connected to any computer system, and accordingly, may be present on a network in a distributed manner. An example of the medium includes a medium configured to store program instructions, including a magnetic medium such as a hard disk, a floppy disk, and a magnetic tape, an optical medium such as a CD-ROM and a DVD, a magnetic-optical medium such as a floptical disk, and a ROM, a RAM, a flash memory, etc. In addition, other examples of the medium may include an app store that distributes applications, a site that supplies or distributes various software, and a recording medium or a storage medium managed by a server.

The methods, operations, or techniques of the present disclosure may be implemented by various means. For example, these techniques may be implemented in hardware, firmware, software, or a combination thereof. Those skilled in the art will further appreciate that various illustrative logical blocks, modules, circuits, and algorithm steps described in connection with the disclosure herein may be implemented in electronic hardware, computer software, or combinations of both. To clearly illustrate this interchangeability of hardware and software, various illustrative components, blocks, modules, circuits, and steps have been described above generally in terms of their functionality. Whether such a function is implemented as hardware or software varies according to design requirements imposed on the particular application and the overall system. Those skilled in the art may implement the described functions in varying ways for each particular application, but such implementation should not be interpreted as causing a departure from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computer, or a combination thereof.

Accordingly, various example logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with instructions stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), magnetic or optical data storage devices, etc. The instructions may be executable by one or more processors, and may cause the processor(s) to perform certain aspects of the functions described in the present disclosure.

Although the examples described above have been described as utilizing aspects of the currently disclosed subject matter in one or more standalone computer systems, aspects are not limited thereto, and may be implemented in conjunction with any computing environment, such as a network or distributed computing environment. Furthermore, the aspects of the subject matter in the present disclosure may be implemented in multiple processing chips or devices, and storage may be similarly influenced across a plurality of devices. Such devices may include PCs, network servers, and portable devices.

Although the present disclosure has been described in connection with some examples herein, various modifications and changes can be made without departing from the scope of the present disclosure, which can be understood by those skilled in the art to which the present disclosure pertains. Further, such modifications and changes are intended to fall within the scope of the claims appended herein.

The invention claimed is:

1. A method for determining a copy number variation profile by using read depth correction, the method being executed by one or more processors and comprising:
acquiring results of whole-genome analysis associated with a target sample collected from a subject, wherein the target sample comprises a formalin-fixed, paraffin-embedded (FFPE) sample and a fresh frozen (FF) sample;
calculating a read depth associated with the target sample for each of a plurality of predetermined bins on genome based on the acquired results of whole-genome analysis;
correcting the read depth associated with the target sample by:
providing, as input to a trained machine learning model, information corresponding to the target sample and the read depth, wherein the trained machine learning model comprises an artificial neural network comprising a plurality of nodes, and wherein weights of the plurality of nodes were trained based on training data comprising data for each of a plurality of samples collected from a plurality of subjects different from the subject, and wherein the plurality of samples include at least one normal cell sample and at least one abnormal cell sample;
receiving, as output from the trained machine learning model, an indication of a correction to the read depth, wherein the correction to the read depth indicates one or more of a magnitude or direction of a change to the read depth;
determining, based on the corrected read depth, a copy number variation profile associated with the target sample;
detecting a change in the copy number variation profile by monitoring the copy number variation profile; and
outputting an indication of the detected change in the copy number variation profile.

2. The method according to claim 1, wherein the target sample includes a normal cell sample and an abnormal cell sample collected from the subject, and
the determining the copy number variation profile includes determining the copy number variation profile based on the read depth associated with the normal cell sample, the read depth associated with the abnormal cell sample, and an allele frequency associated with the target sample.

3. The method according to claim 1, wherein each of the plurality of predetermined bins is associated with each of a plurality of samples collected from a plurality of subjects different from the subject.

4. The method according to claim 3, wherein the correction to the read depth comprises information associated with a direction of correction of read depth for each of the plurality of predetermined bins.

5. The method according to claim 4, wherein the plurality of samples in the training data correspond to a plurality of different.

6. The method according to claim 5, wherein the correcting comprises:
when a distribution of read depths associated with all FFPE samples in the training data and the distribution of read depths associated with all FF samples in the training data are different, the direction of correction for a corresponding bin is set to either positive or negative value; or
when a distribution of read depths associated with all FFPE samples in the training data and the distribution of read depths associated with all FF samples in the training data are not different, the direction of correction for the corresponding bin is set to "0".

7. The method according to claim 4, wherein the correction to the read depth comprises information associated with a magnitude of correction of read depth for each of the plurality of predetermined bins.

8. The method according to claim 7, wherein the plurality of samples in the training data correspond to a plurality of different average of read depths.

9. The method according to claim 7, wherein the correcting the read depth comprises:
determining a correction coefficient for adjusting the read depth by multiplying the direction of correction by the magnitude of correction, wherein the correction coefficient is determined for each of the plurality of predetermined bins, for correcting the read depth associated with the target sample for each of the plurality of predetermined bins.

10. The method according to claim 1, wherein the correcting the read depth further comprises removing noise from the read depth.

11. The method according to claim 1, further comprising:
determining a plurality of wavelet coefficients using a predetermined wavelet and the read depth; and
further correcting the read depth based on the plurality of wavelet coefficients.

12. The method according to claim 11, wherein the predetermined wavelet corresponds to a Haar wavelet.

13. The method according to claim 1, further comprising:
based on an absolute value of a specific wavelet coefficient of a plurality of wavelet coefficients being less than a predetermined threshold, replacing the specific wavelet coefficient with O; or
based on the absolute value of the specific wavelet coefficient being greater than or equal to the predetermined threshold, attenuating the specific wavelet coefficient to a higher degree as a difference between the absolute value and the threshold decreases.

14. The method according to claim 13, wherein the predetermined threshold comprises a first threshold and a second threshold, which is lower than the first threshold, wherein a first level wavelet coefficient has a first specific wavelet coefficient, and a second level wavelet coefficient has a second specific wavelet coefficient, which is higher than the first specific wavelet coefficient, and wherein the first level wavelet coefficient has the first threshold, and the second level wavelet coefficient has the second threshold.

15. A non-transitory computer-readable recording medium storing instructions for execution by the one or more processors that, when executed by the one or more processors, cause the one or more processors to perform the method according to claim 1.

16. The method according to claim 1, further comprising:
predicting response to treatment based on the copy number variation profile; and
determining a different therapeutic approach based on the predicted response.

17. The method according to claim 1, further comprising:
identifying, based on the detected change, a therapeutic approach associated with the subject, wherein the correcting of the read depth associated with the target sample comprises:

performing, based on an identified pattern of read depth distortions, a first correction of the read depth; and performing, based on at least one wavelet parameter, a second correction of the read depth by removing noise from data associated with the FFPE sample.

18. The method according to claim 17, wherein the noise is removed further based on a frequency filtering of at least one filter.

19. A computing device, comprising:

a communication module;

a memory; and one or more processors connected to the memory and configured to execute one or more computer-readable programs included in the memory, wherein the one or more computer-readable programs include instructions for:

acquiring results of whole-genome analysis associated with a target sample collected from a subject, wherein the target sample comprises a formalin-fixed, paraffin-embedded (FFPE) sample and a fresh frozen (FF) sample;

calculating a read depth associated with the target sample for each of a plurality of predetermined bins on genome based on the acquired results of whole-genome analysis;

correcting the read depth associated with the target sample by:

providing, as input to a trained machine learning model, information corresponding to the target sample and the read depth, wherein the trained machine learning model comprises an artificial neural network comprising a plurality of nodes, and wherein weights of the plurality of nodes were trained based on training data comprising data for each of a plurality of samples collected from a plurality of subjects different from the subject, and wherein the plurality of samples include at least one normal cell sample and at least one abnormal cell sample;

receiving, as output from the trained machine learning model, an indication of a correction to the read depth, wherein the correction to the read depth indicates one or more of a magnitude or direction of a change to the read depth;

determining, based on the corrected read depth, a copy number variation profile associated with the target sample;

detecting a change in the copy number variation profile by monitoring the copy number variation profile; and outputting an indication of the detected change in the copy number variation profile.

20. The computing device according to claim 19, wherein the target sample includes a normal cell sample and an abnormal cell sample collected from the subject, and the determining the copy number variation profile includes determining the copy number variation profile based on the read depth associated with the normal cell sample, the read depth associated with the abnormal cell sample, and an allele frequency associated with the target sample.

* * * * *